(12) United States Patent
Fares et al.

(10) Patent No.: US 8,871,197 B2
(45) Date of Patent: Oct. 28, 2014

(54) **EXTRACTS OF *CYATHUS STRIATUS* MUSHROOMS, PHARMACEUTICAL COMPOSITIONS COMPRISING THEM AND A NEW *CYATHUS STRIATUS* STRAIN**

(75) Inventors: Fuad Fares, Hourfish (IL); Lital Shavit, Qiryat Motzkin (IL); Solomon P. Wasser, Nesher (IL)

(73) Assignee: Carmel-Haifa University Economic Corporation Ltd., Mount Carmel, Haifa (IL)

( * ) Notice: Subject to any disclaimer, the term of this patent is extended or adjusted under 35 U.S.C. 154(b) by 0 days.

(21) Appl. No.: 13/701,673

(22) PCT Filed: Jun. 2, 2011

(86) PCT No.: PCT/IL2011/000434
§ 371 (c)(1),
(2), (4) Date: Feb. 12, 2013

(87) PCT Pub. No.: WO2011/151831
PCT Pub. Date: Dec. 8, 2011

(65) Prior Publication Data
US 2013/0142820 A1  Jun. 6, 2013

Related U.S. Application Data
(60) Provisional application No. 61/351,078, filed on Jun. 3, 2010.

(51) Int. Cl.
| | | |
|---|---|---|
| *A01N 63/00* | (2006.01) | |
| *A01N 63/04* | (2006.01) | |
| *A01N 65/00* | (2009.01) | |
| *A61K 36/06* | (2006.01) | |
| *A61K 36/09* | (2006.01) | |
| *A61K 36/07* | (2006.01) | |
| *C12R 1/645* | (2006.01) | |
| *C12N 1/14* | (2006.01) | |

(52) U.S. Cl.
CPC .............. *A61K 36/07* (2013.01); *C12R 1/645* (2013.01); *C12N 1/14* (2013.01)
USPC .................................. 424/93.5; 424/195.15

(58) Field of Classification Search
None
See application file for complete search history.

(56) References Cited

U.S. PATENT DOCUMENTS

| | | | | |
|---|---|---|---|---|
| 3,281,330 A | * | 10/1966 | Fonken et al. | 435/248 |
| 2005/0038254 A1 | * | 2/2005 | Michels et al. | 546/217 |

OTHER PUBLICATIONS

Petrova et al. Mol. Biol. rep., vol. 34, 2007, p. 145-154.*
Fujioka et al.,Clin Cancer Res 2003;9:346-354.*
Anke et al., Z. Naturforsch. 57c, 263-271 (2002).*
Petrova et al., "Fungal Substances as Modulators of NF—[Kappa] B Activation Pathway" Molecular Biology Reports (2007) 34(3):145-154.
Kang et al., "Cyathuscavins A, B, and C, new free radical scavengers with DNA protection activity from the Basidiomycete *Cyathus stercoreus*", Bioorganic & Medicinal Chemistry Letters,(2008) 18(14):4047-4050.
Liu et al., "Antimicrobial activities of selected *Cyathus* species," Mycopathologia (2004) 157:185-189.
Kang et al., "Cyathusals A, B, and C, Antioxidants from the Fermented Mushroom *Cyathus stercoreus*," J. Nat. Prod. (2007) 70:1043-1045.

* cited by examiner

*Primary Examiner* — Chris R Tate
*Assistant Examiner* — Douglas F White
(74) *Attorney, Agent, or Firm* — Volpe and Koenig, P.C.

(57) ABSTRACT

A new and distinct variety of higher Basidiomycetes mushroom *Cyathus striatus* HAI-1302, and extracts thereof are provided. These extracts as well as pharmaceutical composition comprising them are capable of inhibiting growth of cancer cells, arresting cancer cell cycle, reducing DNA synthesis in cancer cells and inducing apoptosis in cancer cells, and are thus useful for the treatment of cancer.

10 Claims, 14 Drawing Sheets

Control

Cyathus striatus extract (10 µg/ml)

Cyathus striatus extract concentration (µg/ml)

Cyathus striatus extract concentration (µg/ml)

Pro-casp-9 (47kDa)

Cleaved casp-9 (37kDa and 35kDa)

Cleaved casp-9 (17kDa)

Pro-casp-3 (35kDa)

Cleaved casp-3 (17kDa)

EXTRACTS OF *CYATHUS STRIATUS* MUSHROOMS, PHARMACEUTICAL COMPOSITIONS COMPRISING THEM AND A NEW *CYATHUS STRIATUS* STRAIN

This application is a 35 U.S.C. §371 national phase application of PCT/IL2011/000434, which was filed Jun. 2, 2011 and is incorporated herein by reference as if fully set forth.

TECHNICAL FIELD

The present invention relates to extracts obtained from a medicinal mushroom of the genus *Cyathus striatus*, to a new and distinct strain designated *Cyathus striatus* CBS 126585 and to extracts thereof, to pharmaceutical compositions comprising the extracts and to methods for treatment of pancreatic and other types of cancer using the pharmaceutical compositions.

BACKGROUND ART

Natural products have been the most significant source of drugs and drug leads in history. Many conventional therapies have been developed from nature-derived materials. Their dominant role in cancer chemotherapeutics is clear, with about 74% of anticancer compounds being either natural products or natural product-derived. It is estimated that approximately 25% of the drugs prescribed worldwide, at present, come from plants and 60% of anti-tumor/anti-infectious drugs, already on the market or under clinical investigations, are of natural origin (Wang et al., 2007).

Higher Basidiomycetes mushrooms (HBM) represent a major and still largely unexploited source of new pharmaceutical products. Of approximately 15,000 known species, 2,000 are safe for human consumption, and about 650 of them possess medicinal properties. Of about 650 mushroom species with known medicinal properties, only about 20 species are in use at the present. Most traditional knowledge about medicinal properties of HBM arrives from the Far East (China, Japan, Korea, and Russian Siberia). Many pharmaceutical substances with potent and unique properties have recently been extracted from mushrooms. Unique anticancer remedies were prepared from these extracts such as polysaccharides lentinan, krestin, and schizophyllan (Mizuno, 1999).

Present studies suggest that extracts and active agents obtained from HBM act as immunomodulators or as biological response modifiers (BRM). They help the body to strengthen itself and fight off illness by maintaining physiological homeostasis and restoring the body's Host Defense Potentiators (HDP), which can have immune system enhancement properties. This benefit is one of the reasons why they are currently used as adjuncts to cancer treatment in many countries. In Japan, Russia, China, and the USA several polysaccharide anticancer and immunomodulating agents have been developed from the fruiting body, mycelia, and culture medium of various medicinal mushrooms (*Lentinus edodes, Ganoderma lucidum, Schizophyllum commune, Trametes vesicolor, Inonotus obliquus, Hypsizigus marmoreus,* and *Flammulina velutipes*) (Ikekawa, 2001).

Many edible mushrooms were used in traditional folk medicine including *Lentinus edodes* (shiitake mushroom). *Grifola frondosa* (maitake), *Hericium erinaceus, Flammulina velutipes, Pleurotus ostreatus,* and *Tremella mesenterica* which are also sources of relatively pure bioactive compounds for medical usage, while other non-edible species, such as *Ganoderma lucidum, Schizophyllum commune,* and *Trametes versicolor,* are used only for their medicinal properties.

Fungal metabolites have been gaining scientific interest as they were found to possess medicinal properties. Many studies on medicinal mushrooms proved their potential not only as dietary supplements and immunoenhancers (Wasser & Weis, 1999a, b) but also as modulators of various cellular responses (Zaidman et al., 2005).

The diversification of medicinal higher fungi represents great potential for new drugs. As known, cancer chemotherapy has relied mostly on cytotoxic drugs, which inhibit tumor cell proliferation and cause cell death. Cytotoxic activities against various tumor cell lines of higher fungi secondary metabolites were widely investigated in the past decades.

Low-molecular-weight (LMW) substances with fungal origin can penetrate the cell membrane and interfere, in particular, with cellular pathways linked to processes such as inflammation, carcinogenesis, cell differentiation and survival, metastasis, etc. On the basis of these facts, medicinal mushrooms were established as a novel and promising source for natural therapeutics that can be successfully applied in the treatment of different diseases, including cancer (Smith et al., 2002). Extracts from many mushrooms, as well as specific active substances isolated from such extracts (e.g. Yassin et al., 2003), have been shown to exhibit anti-cancer activity.

For example, Muller et al. (2006) found that methanol: water extracts from fruiting bodies of *G. lucidum* induce apoptosis for each of the 26 panel of human cancer cell lines examined, in a dose-dependent manner.

Wu et al. (2006) used ethyl acetate extracts from the mycelium of Cordyceps sinensis to show the inhibitory effect on various cancer cell lines. They projected the inhibitory effect to ergosterol and related compounds present in the extract.

Lu et al. (2004) used ethanol:water extracts of the *Coriolus vesicolor* fruiting bodies to inhibit the proliferation of Burkitt's lymphoma B-cell line (HL-60) and human acute promyelocytic leukemia cell lines (NB-4), in a dose-dependent manner, with more than 90% suppression, and no significant suppression on the proliferation of normal liver cell lines (WRL).

Pancreatic ductal adenocarcinoma (PDAC) is one of the deadliest of all solid malignancies. It is the thirteenth most common cancer worldwide and one of the leading causes of cancer death with 232,000 new cases each year and 213,000 deaths. In the United States and Israel, pancreatic cancer is the fourth leading cause of cancer related mortalities. In the year 2010 an estimated 43,140 patients were diagnosed with pancreatic cancer; 36,800 patients died of their disease in the US alone.

PDAC is a disease with very poor prognosis mainly because of insensitivity to most standard therapies including chemotherapy, radiotherapy, and immunotherapy. Therefore, surgical resection offers, at the moment, the only potential prospect for a cure.

For all stages combined, the 1- and 5-year relative survival rates of PDAC are 24% and 5%, respectively. Even for those people diagnosed with local disease, the 5-year survival is merely 20%. These unfortunate statistics reflect the advanced stage at which most patients with pancreatic cancer are diagnosed and the paucity of effective chemotherapeutic regimens for advanced disease.

To our knowledge, no previous publication disclosing the activity of *Cyathus striatus* mushroom extracts on pancreatic cancer cells exists. We have found some data on other members of the genus *Cyathus*, e.g., *Cyathus bulleri* (Kang et al., 2007), *Cyathus stercoreus*, *Cyathus olla*, *Cyathus africanus*, *Cyathus colensoi*, *Cyathus gansuensis*, *Cyathus* sp.39, *Cyathus pallidus*, *Cyathus intermedius*, *Cyathus* sp.34, *Cyathus* sp. 37, *Cyathus nigroalbus*, *Cyathus* sp. 73, and *Cyathus luxiensis* (Liu & Zhang, 2004). Most of the data pertains to antimicrobial or antifungal properties. The mushroom *Cyathus striatus* was investigated in our lab for the first time for its anticancer properties. In an extensive screening of 242 crude mushroom extracts, Petrova et al. (2007) from our lab demonstrated a potent growth-inhibitory effect of some of the extracts, e.g. from *C. striatus*, on MCF7-human breast cancer cell line, PC3 and DU145-human androgen-independent prostate cancer, 9L-rat glioblastoma, and Baf3/p185 Bcr-Abl-B-lymphocytes, a laboratory model of CML. Petrova also found *C. striatus* to modulate IκBα levels even in the lowest concentration used (5 and 1 μg/ml) and demonstrated the ability to inhibit both IκBα phosphorylation and degradation (Petrova et al., 2007).

SUMMARY OF INVENTION

A novel and distinct variety of the higher Basidiomycetes mushroom *Cyathus striatus* has been isolated by the inventors and it is shown herein that an extract of this mushroom is effective in inhibiting growth of, and inducing apoptosis in, pancreatic cancer cells. Other varieties of *C. Striatus* are known to be rich in nutraceutical agents and biologically active compounds and extracts thereof have been shown to be effective in killing breast cancer cells, human androgen-independent prostate cancer cells, rat glioblastoma cells, and a laboratory model of CML cells. Consequently, the biomass and extracts of this novel mushroom is efficacious in treating cancer, in particular pancreatic cancer, and can be used in food supplement, pharmaceutical, prebiotic, nutraceutical, beverage or cosmetic products.

The present invention relates therefore, in one aspect, to the new and distinct variety of higher Basidiomycetes mushroom *Cyathus striatus* CBS 126585, an extract obtained from the culture liquid of a submerged mycelium culture of the mushroom, and a pharmaceutical composition comprising a pharmaceutically acceptable carrier and said extract. In certain embodiments, the extract is for use in treating cancer, in particular pancreatic cancer. In a further aspect, the present invention relates to a pure submerged mycelial culture of *Cyathus striatus* CBS 126585.

In another aspect, the present invention provides an extract obtained from a higher Basidiomycetes mushroom *Cyathus striatus* for use in treatment of pancreatic cancer. In certain embodiments, the extract is obtained from a new and distinct variety of higher Basidiomycetes mushroom *Cyathus striatus* HAI-1302, deposited under The Budapest Treaty with the Centralbureau voor Schimmelcultures (CBS) under Accession No. CBS 126585 (hereinafter *Cyathus striatus* CBS 126585).

In still another aspect, the present invention is directed to a method for treating pancreatic cancer, comprising administering to a patient in need a therapeutically effective amount of an extract obtained from higher Basidiomycetes mushroom *Cyathus striatus*.

The present invention is also directed to a method for treating cancer such as pancreatic cancer, breast cancer, chronic myelogenous leukemia (CML) and prostate cancer, in particular pancreatic cancer, comprising administering to a patient in need a therapeutically effective amount of an extract obtained from *Cyathus striatus* CBS 126585.

Lane 2: HPAF-II control untreated cells, Lane 3: HPAF-II treatment, Lane 4: PL45 control untreated cells, Lane 5: PL45 treatment.

Figure 7A:
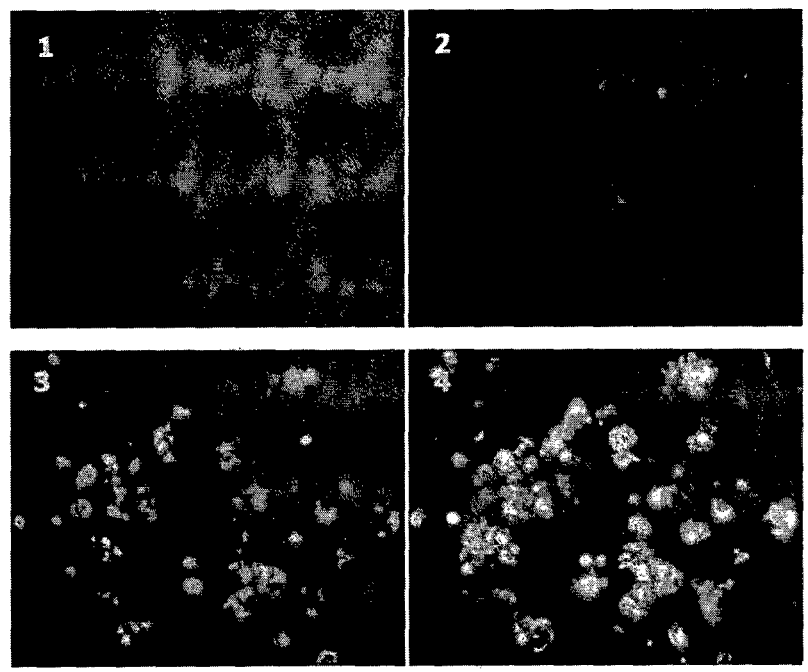
Figure 7B:
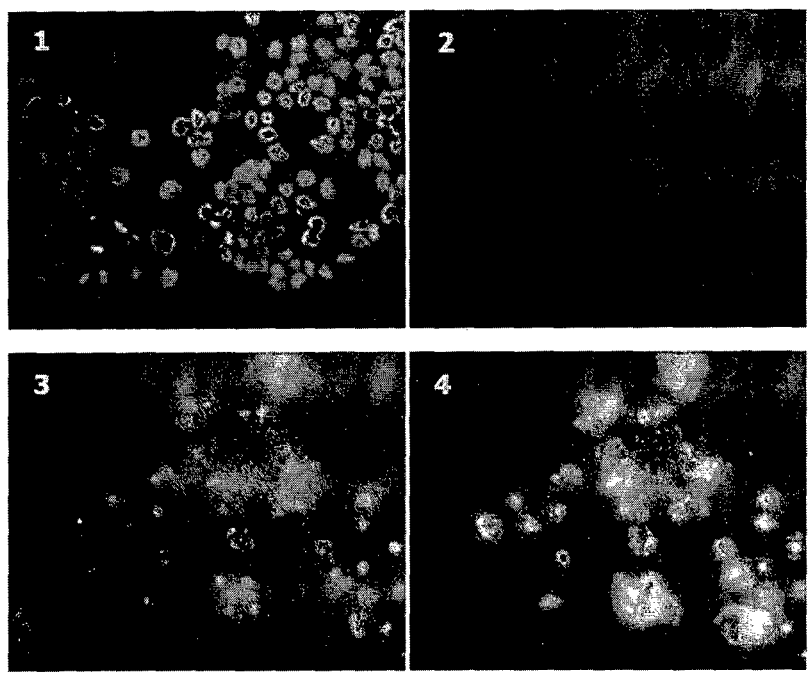

FIGS. 7A-B depict the effect of *C. striatus* C.L EAC extract on apoptosis induction using TUNEL and DAPI staining of (A) HPAF-II and (B) PL45 cells. Cells were counted and seeded on chamber slides (Nunc, Denmark) ($25 \times 10^3$ cells/ml). On the next day, cells were treated with *C. striatus* C.L extract for 24 h at a concentration of 10 µg/ml. At the end of treatment, cells were stained with TUNEL and DAPI and analyzed under a fluorescent microscopy (×400 magnification). 1. DAPI control; 2. TUNEL control; 3. DAPI with 10 µg/ml *C. striatus* C.L EAC extract; 4. TUNEL with 10 µg/ml *C. striatus* C.L EAC extract.

Figure 8A:
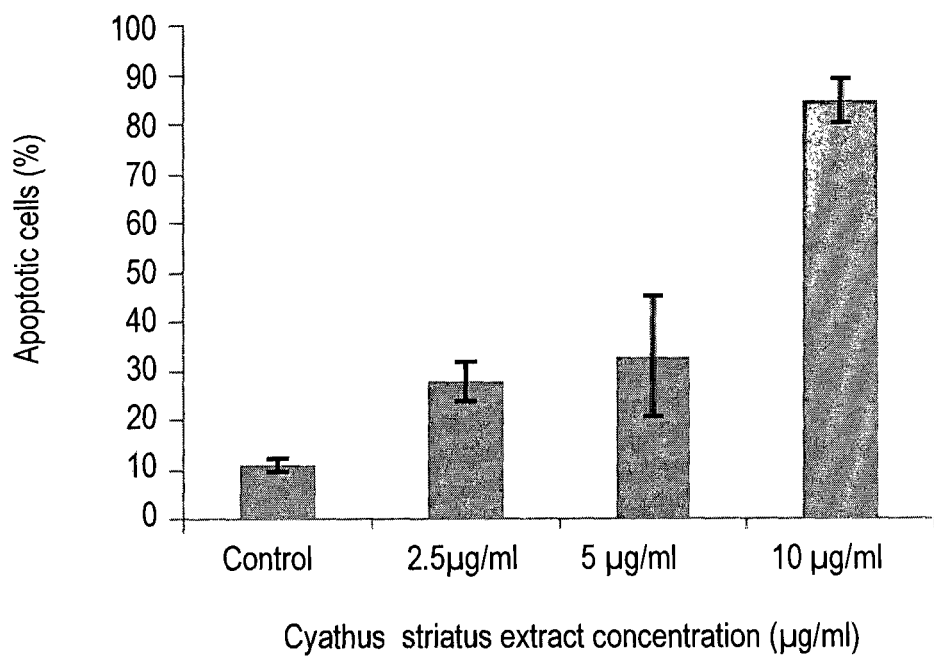
Figure 8B:
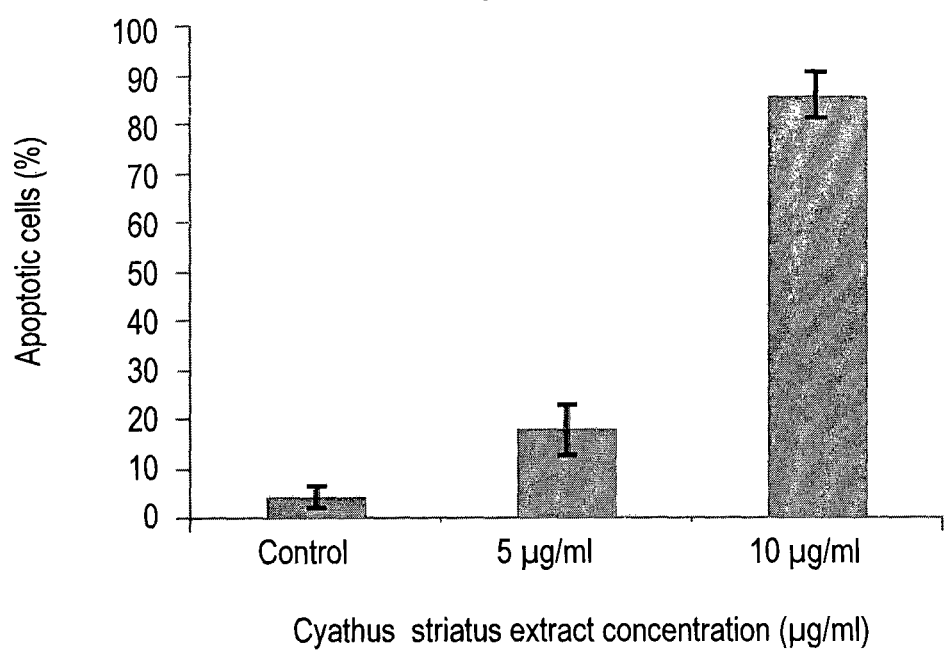

FIGS. 8A-B show the effect of *C. striatus* C.L EAC extract on apoptosis induction according to Annexin V-PI double staining by flow cytometry of HPAF-II cells (A) and PL45 cells (B). Cells were treated with different extract concentrations (Control (0 µg/ml), 2.5, 5 or 10 µg/ml) for 4 h, and $5 \times 10^5$ cells/ml were counted and collected for the analysis. Apoptotic cells as percent of total cells observed is presented. All results represent means±SEM of three independent experiments.

Figure 9A:
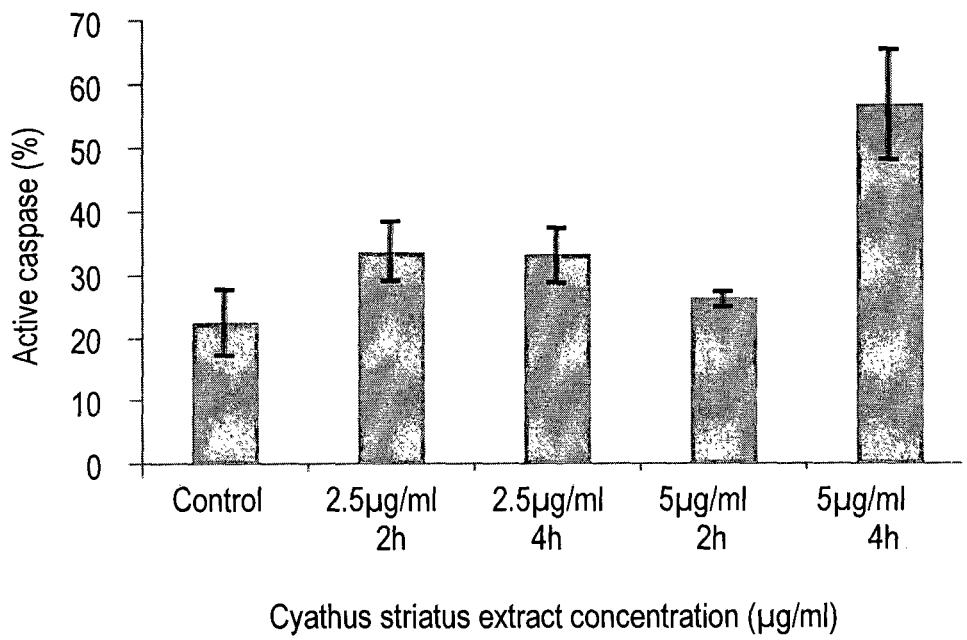
Figure 9B:
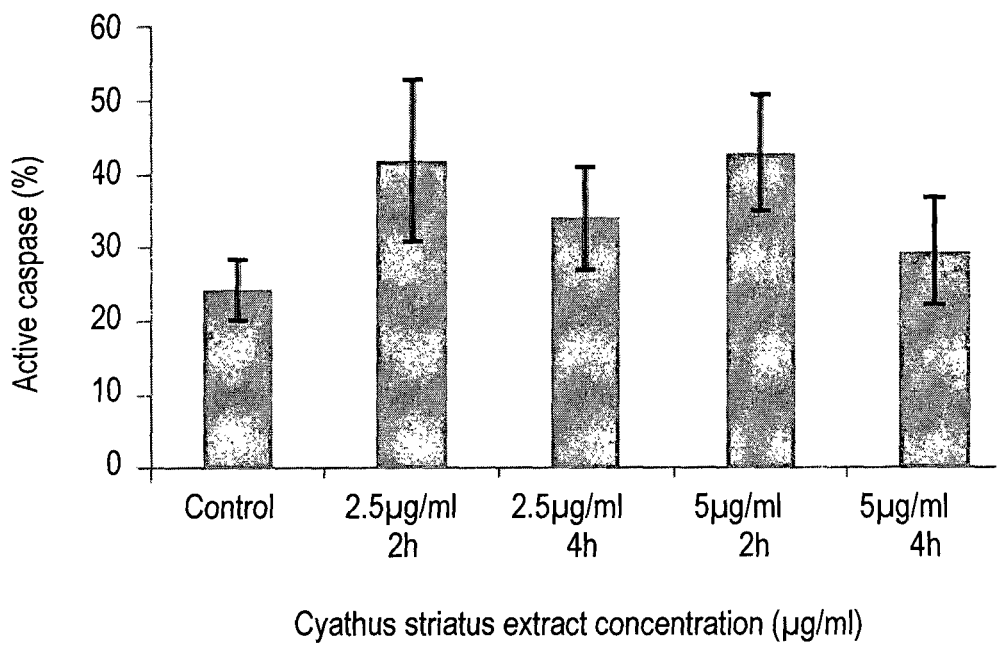

FIGS. 9 A-B show the effect of *C. striatus* C.L EAC extract on caspase 9 activity of HPAF (A) and PL45 (B) cells by flow cytometry. $1 \times 10^6$ cells/ml were incubated with different concentrations (Control (0 µg/ml), 2.5 or 5 µg/ml) of *C. striatus* extract for 2 or 4 h. Caspase-9 positive cells as percent of total cells observed is presented. All results represent mean±SEM of three independent experiments.

Figure 10A:
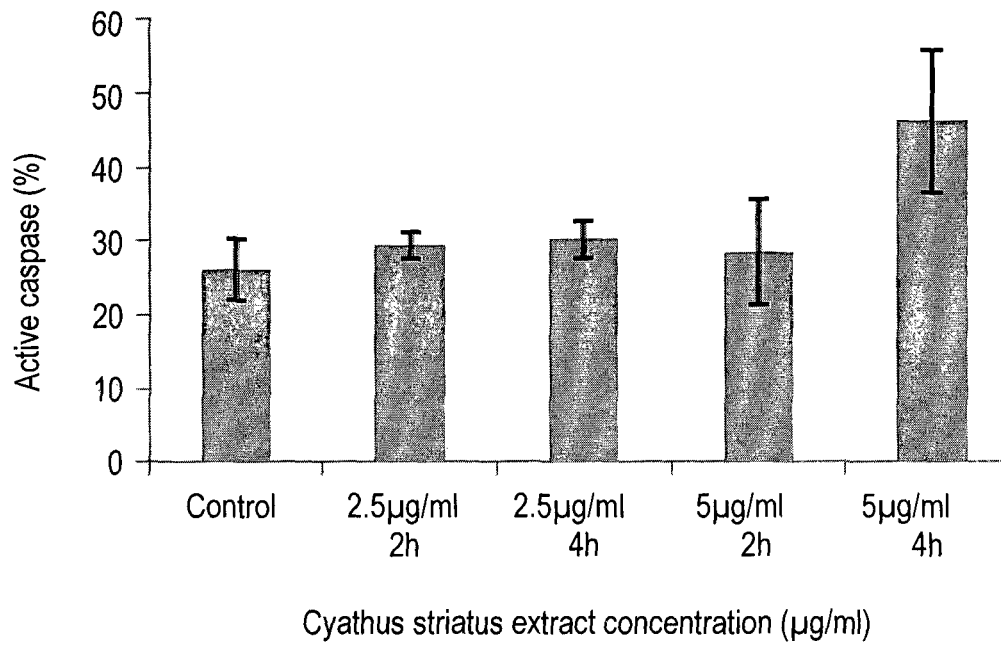
Figure 10B:
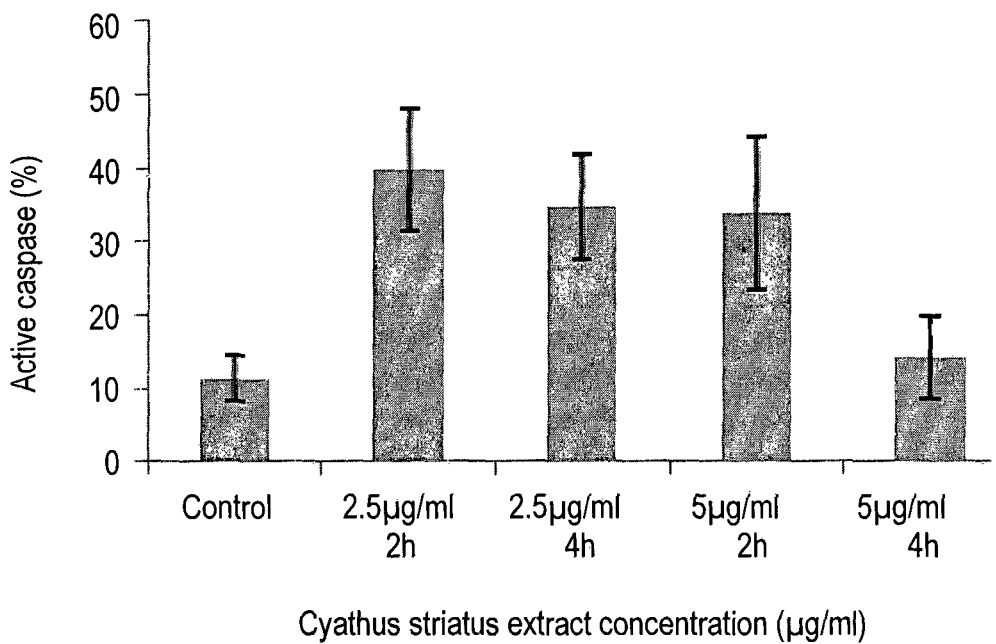

FIGS. 10A-B show the effect of *C. striatus* C.L EAC extract on caspase 8 activity of HPAF (A) and PL45 (B) cells by flow cytometry. $1 \times 10^6$ cells/ml were incubated with different concentrations (Control (0 µg/ml), 2.5 or 5 µg/ml) of *C. striatus* extract for 2 or 4 hrs. Caspase-8 positive cells as percent of total cells observed is presented. All results represent mean±SEM of three independent experiments.

Figure 11:
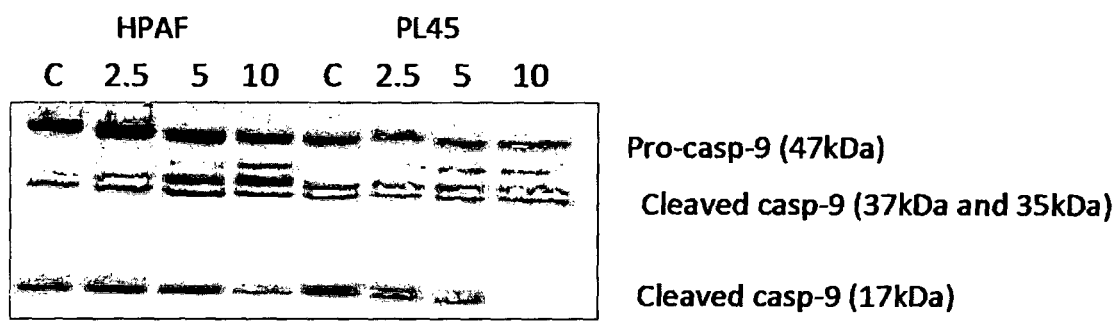

FIG. 11 shows the effect of *C. striatus* C.L EAC on apoptosis induction according to expression of pro-caspase-9 and cleaved caspase-9. Different concentrations (C (0 µg/ml), 2.5, 5 and 10 µg/ml) of *C. striatus* C.L extract were added to $2 \times 10^6$ HPAF and PL45 cells for 12 h. At the end of treatment, treated and control untreated cells were collected, proteins were extracted, and identical samples of 60 µg protein were subjected to Western blot analysis. Data are representative of three independent experiments.

Figure 12:
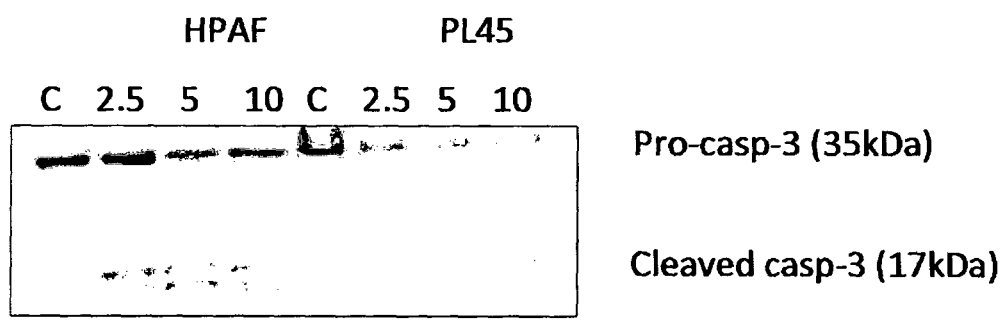

FIG. 12 shows the effect of *C. striatus* C.L EAC on apoptosis induction according to expression of pro-caspase-3 and cleaved caspase-3. Different concentrations (C (0 µg/ml), 2.5, 5, and 10 µg/ml) of *C. striatus* C.L extract was added to $2 \times 10^6$ cells for 12 h. At the end of treatment, treated and control untreated cells were collected, proteins were extracted, and identical samples of 60 µg protein were subjected to Western blot analysis. Data are representative of three independent experiments.

DETAILED DESCRIPTION OF THE INVENTION

The present invention is directed inter alia to extracts and active agents obtained from *Cyathus striatus* mushrooms.

Although most bioactive substances isolated from mushrooms are high-molecular-weight (HMW) polysaccharides, our interest is in low-molecular-weight (LMW) compounds capable of exhibiting antitumor activity. The search for such compounds was focused on the higher Basidiomycetes mushroom *Cyathus striatus*, in view of the inventors' previous experience with this mushroom. For example, Petrova et al. (2007) demonstrated a potent growth-inhibitory effect of extracts from *C. striatus*, on breast cancer cells, human androgen-independent prostate cancer cells, rat glioblastoma cells, and a laboratory model of CML cells. Petrova et al. also found *C. striatus* to modulate IκBα levels and demonstrated the ability to inhibit both IκBα phosphorylation and degradation.

Presently, a new and distinct variety of the mushroom was isolated and characterized (see Example 1). Extracts obtained from this mushroom was shown herein to be extremely toxic to pancreatic cancer cells (see Example 2).

Thus, in some aspects, the present invention relates to a new and distinct variety of higher Basidiomycetes mushroom *Cyathus striatus* HAI-1302, deposited under The Budapest Treaty with the Centralbureau voor Schimmelcultures (CBS) under Accession No. CBS 126585 (hereinafter *Cyathus striatus* CBS 126585), extracts obtained from *Cyathus striatus* CBS 126585, and to a pharmaceutical composition comprising the extract and a pharmaceutically acceptable carrier.

In other aspects, the present invention relates to an extract obtained from higher Basidiomycetes mushroom *Cyathus striatus* for use in the treatment of cancer, in particular pancreatic cancer, and to a pharmaceutical composition comprising a pharmaceutically acceptable carrier and the extract, wherein the pharmaceutical composition is for treatment of cancer, in particular pancreatic cancer.

The term "treating cancer" as used herein refers to the inhibition of the growth of cancer cells. Preferably such treatment also leads to the regression of tumor growth, i.e. to the decrease in size or complete regression of the tumor. In preferred embodiments, the term refers to treatment and alleviation or complete cure of disseminated tumors, namely, of metastases.

The extracts of the present invention are obtained from the culture liquid of a submerged mycelium culture of the mushroom or from the biomass of the submerged mycelium culture. In certain embodiments, the extracts are obtained from the culture liquid of a submerged mycelium culture of the mushroom. The extraction is performed with an extraction solvent comprising one or more organic solvents such as, without being limited to, ethyl acetate, ethanol, chloroform, methanol, acetonitrile, hexane, cyclohexane, isooctane and dichloromethane. In certain embodiments, the organic solvent is selected from ethyl acetate, ethanol and chloroform.

The extracts obtained as described above are concentrated and may be purified. Concentration can be carried out by conventional techniques such as thermal, decompressing thermal, activated carbon or ion exchange resin methods. The concentrated extract is then purified to yield a purified extract of one or more purified compositions using standard techniques such as column chromatography, fractional distillation, preparative TLC (thin layer chromatography), preparative HPLC (high performance liquid chromatography), CPC (centrifugal partition chromatography) or other techniques known to those skilled in the art. After concentration and purification, the product is dried by any conventional technique such as air-drying, hot-blast drying, spray drying, and freeze-drying methods. The concentrated extract is dissolved in dimethyl sulfoxide (DMSO).

The extracts obtained from the *C. striatus* mushrooms are rich in low-molecular weight compounds such as alkaloids, terpenoids, glycosides, flavonoids, terpenes and phenols, obtained from culture liquid or mycelium of the mushrooms. low-molecular-weight mushroom organic substances have their origins as derivatives from many intermediates in primary metabolism. The upper molecular weight limit for a small molecule is approximately 800 Daltons.

It has been found in accordance with the present invention that the extract obtained from the culture liquid of a submerged mycelium culture of the novel mushroom *Cyathus striatus* CBS 126585 contains most of the growth-inhibiting or cytotoxic activity of the mushroom and that the extraction of the culture liquid with ethyl acetate results in the most active extract. Consequently, in one embodiment, the organic extraction solvent used to extract the culture medium of the mushroom mycelium is ethyl acetate.

It has also been found in accordance with the present invention that the active agents comprised in the extract exert their activity at least by arrest of the cell cycle, reduction in DNA synthesis in cancer cells, and induction of apoptosis in cancer cells by activation of both the caspase 8 and the caspase 9 pathways followed by the activation of the executing caspase 3 pathway.

Thus, in certain embodiments, the extract inhibits growth of cancer cells, arrests cancer cell cycle, reduces DNA synthesis in cancer cells, and/or induces apoptosis in cancer cells. This is of great importance because it is well known that characteristic changes such as deregulation of the cell cycle machinery and acquirement of self-sufficiency in growth signals, insensitivity to growth inhibitory signals, ability to evade apoptosis, invade tissue form metastases, and to sustain angiogenesis are hallmarks of the majority of cancers and can also be found in Pancreatic ductal adenocarcinoma.

One of these routes of changes, the evasion of apoptosis, is a fundamental mechanism in cancer treatment. Apoptosis, or programmed cell death, is a central regulator of normal tissue homeostasis. The physiological "cell suicide" program is essential for the elimination of redundant, damaged, and infected cells. Disturbed apoptosis is involved in the pathogenesis of multiple diseases, especially cancer. The acquisition of mechanisms to evade apoptosis is a hallmark of cancer, with both the loss-of-function of pro-apoptotic signals and gain-of-function of anti-apoptotic mechanisms contributing to tumorigenesis and the cancer phenotype.

Most chemotherapies act by the induction of apoptosis. Therefore, the evasion of apoptosis is mainly responsible for the insufficiency of current therapies. Tumor cells use multiple pathways to escape apoptosis. Defective apoptotic mechanisms allow genetically unstable cancer cells to avoid elimination and confer resistance to chemotherapy.

As such, modulating the apoptotic pathways likely represents a propitious strategy for inducing tumor-cell death and increasing responses to chemotherapy, radiotherapy, and even targeted therapies. Therefore, agents that can restore apoptosis in cancer cells hold promise for therapy and have been the focus of many preclinical drug discovery studies.

Execution of apoptosis relies on a group of cysteine proteases, the caspases (Degterev et al., 2003). Caspases are synthesized as proforms and become activated by cleavage next to aspartate residues. Since caspases cleave and activate each other, an amplification mechanism through a protease cascade exists, assuring proper execution of apoptotic cell death (Degterev et al., 2003).

There are two alternative pathways to initiate apoptosis through the initiator caspases (caspase-8, -9, and -10), and both ultimately activate the executioner caspases-3, -6, and -7. The first pathway is the intrinsic or mitochondrial pathway, which involves an imbalance of pro- and anti-apoptotic members of the BCL-2 protein family. The second pathway is the extrinsic pathway and is mediated by different death receptors on the cell surface (Debatin et al., 2004; Fas et al., 2006; Wajant et al., 2006).

A most beneficial feature of the extract, as shown in Example, 2, is that it is capable of inducing apoptosis in pancreatic cancer cells. Since a multitude of active agents are comprised in the extract of the present invention that may induce apoptosis by different pathways, it is likely that the cells in a cancer tumor exposed to the extract would not have enough time to develop mutated proteins that would render all these pathways resistant to the active agents in the extract. In view of this, and the fact that extracts from other *C. striatus* strains have been shown to be efficacious against a number of cancer types, the extracts and pharmaceutical compositions of the present invention are useful for treating cancer such as pancreatic cancer, breast cancer, chronic myelogenous leukemia (CML) and prostate cancer.

In certain embodiments, the extract obtained from higher Basidiomycetes mushroom *Cyathus striatus* is for treating pancreatic cancer such as ductal adenocarcinomas, acinar cell carcinomas, adenosquamous carcinomas, colloid carcinomas, giant cell tumors, hepatoid carcinomas, intraductal papillary-mucinous neoplasms, mucinous cystic neoplasms, pancreatoblastomas, serous cystadenomas, signet ring cell carcinomas, solid and pseudopapillary tumors, undifferentiated carcinomas, undifferentiated carcinomas with osteoclast-like giant cells and pancreatic endocrine tumors.

In other certain embodiments, the extract obtained from the novel and distinct variety *Cyathus striatus* CBS 126585, is for treating cancer, such as pancreatic cancer, breast cancer, chronic myelogenous leukemia (CML) and prostate cancer. In particular, the pharmaceutical composition comprising an extract obtained from *Cyathus striatus* CBS 126585 is for treating pancreatic cancer.

In related aspects, the present invention is directed to methods for treating cancer, such as pancreatic cancer, breast cancer, chronic myelogenous leukemia (CML) and prostate cancer, comprising administering to a cancer patient a therapeutically effective amount of an extract of the present invention or a pharmaceutical composition comprising this extract.

The pharmaceutical compositions, depending on their intended use, may be adapted for oral, intravenous, subcutaneous, intraarticular, intramuscular, inhalation, intranasal, intrathecal, intraperitoneal, intradermal, transdermal or enteral administration.

The present invention is further directed to a pure submerged mycelial culture of *Cyathus striatus* CBS 126585, and to a biomass and an extract obtained from the pure submerged mycelial culture, which are rich in nutraceutical agents and biologically active compounds including antibiotics, carbohydrates, proteins rich in essential amino acids, vitamins, lipids rich in essential fatty acids, antioxidant agents and minerals.

In further aspects, the present invention provides a composition comprising the biomass or an extract obtained from the pure submerged mycelial culture, or a mixture of said biomasses or extracts, and food supplement, pharmaceutical, prebiotic, nutraceutical, beverage and cosmetic products comprising this composition. Furthermore, a pharmaceutical composition comprising a pharmaceutically acceptable carrier and the composition comprising the biomass or an extract obtained from the pure submerged mycelial culture is provided.

Also, the invention contemplates the use of the extracts and biomasses of the invention in mixtures with biomasses and/or extracts of other medicinal mushrooms such as, but not limited to, *Shitake, Coprinus* and *Tremella*.

The invention will now be illustrated by the following non-limiting examples:

EXAMPLES

Materials and Methods

Preparations of Mushroom Extracts

Mycelial culture of the investigated mushroom species was obtained from the culture collection (HAI) of the Institute of Evolution, University of Haifa, Israel. The mushroom strain was grown first on a solid medium and then transferred onto submerged conditions, following Yassin et al. ((2003) *Int J Med Mushr*, 5:261-276). The strain was grown in submerged conditions for biomass production for 10 days, in order to reach the growth stage of secondary metabolite production. Biomass extraction was performed according to Yassin et al. (2003; see above), with the exception of the solvents used. In this study, the obtained fungal biomass was extracted with the following organic solvents (Frutarom, Israel): ethyl alcohol (EAL), ethyl acetate (EAC), and chloroform (CHL). Culture liquid (CL) was extracted with EAC in the ratio of 1 (CL):500 ml (EAC) (Khan et al., (2001) *Pakistan J Biol Sci*, 4(11): 1374-1376).

The dried extract was diluted at a concentration of 50 mg/ml with 99.9% dimethyl sulfoxide (DMSO) (Sigma-Aldrich, St Louis, Mo., USA) and kept at −20° C.

Cell Cultures

The human pancreatic cancer cell lines HPAF-II and PL45 (ATCC, Rockville, Md., USA) were maintained in MEM-EAGLE and DMEM medium, respectively, with 1% L-glutamine supplemented, 10% fetal calf serum (FCS), and 1% PenStrep (penicillin+streptomycin) (Biological industries, Kibbutz Beit Haemek, Israel). The HPAF-II cell line was supplemented with an additional 1% sodium pyruvat, and PL45 cell line was supplemented with an additional 1% L-glutamine. Cells were grown in a humidified incubator at 37° C. with 5% $CO_2$ in air and fed twice a week with fresh medium.

Cytotoxicity Assays

XTT assay. Evaluation of fungal extracts' effect on cell line viability was performed by XTT ((sodium 3'-[1-(phenylaminocarbonyl)-3,4-tetrazolium]-bis(4-methoxy-6-nitro) benzene sulfonic acid hydrate)) assay (Biological Industries). HPAF-II and PL45 cells ($10^4$) were seeded in 100 µl of medium, using 96-well plates. After 24 hours, fungal extracts were added in several concentrations: 1, 2.5, 5, 7.5, 10, 25, and 50 µg/ml for 24, 48, and 72 hours. Control wells were medium treated wells. After 24 hours, viability levels were determined according to the manufacturer's instructions using an Elisa reader (BioTek) at 450 nm wave and subtracted from the reference absorbance at 620 nm. Experiments were repeated 2-5 times independently and conducted in at least 3 replicates. Data are presented as the average proliferation percentage of the respective control.

Crystal violet assay. Crystal violet assay was performed for the evaluation of the effect of fungal extracts on cell viability as well. HPAF-II and PL45 cells ($6\times10^4$) were seeded in 500 µl of medium, using 24-well plates. After 24 h, fungal extracts were added in several concentrations: 1, 2.5, 5, 7.5, 10, 25, and 50 µg/ml for 24, 48 and 72 hours. Subsequently growth medium and fungal extracts were washed with 0.9% NaCl, and then cells were fixed with 96% ethanol for 10 minutes. Crystal violet dye (0.05%) in 20% ethanol was added for 30 minutes. After cells were dyed, the residue dye was removed, and plates were washed 5-7 times with tap water and left for evaporation of residue water. Then, 400 µl 0.1% acetic acid in 50% ethanol was added to each well for the elicitation of the dye from the cell's nucleus. The number of living cells is proportional to the amount of dye. Strength of dye was measured using Elisa reader (BioTek) at 595 nm. Experiments were repeated 3 times independently and conducted in at least 3 replicates. Data are presented as average percentage of the respective control.

Lactate dehydrogenase (LDH) leakage assay. LDH is a cytoplasmic enzyme that catalyzes the oxidation of L lactate to pyruvate with $NAD^+$ as a hydrogen acceptor, the final step in the metabolic chain of anaerobic glycolysis. The extracellular appearance of LDH serve as a marker for tissue lysis since cell damage, such as necrosis, causes a rise of LDH in the cells' medium (Moran and Schnellmann, 1996). In order to exclude the possibility for necrotic effects of the extract on the cell lines, lactate LDH leakage into the medium was measured in aliquots of the extracellular fluid of each sample, as described previously (Goeptar et al., 1994).

DNA synthesis. 5-Bromo-2-uridine Labeling Kit (BrdU) (Roche Applied Science, USA) is a method based on the incorporation of BrdU to proliferating cells. BrdU was added to the cell's culture and was incorporated into newly synthesized DNA of replicating cells, substituting for thymidine during DNA replication. Monoclonal antibodies labeled with peroxidase specific for BrdU are used to detect the incorporated BrdU. The enzyme peroxidase catalyzes the cleavage of the peroxidase substrate that was added to the cells' culture and produces a color reaction, thus indicating cells that were actively replicating their DNA. The color reaction can be measured by Elisa reader, 492 nm and a background absorption of 690 nm. HPAF-II and PL45 cells ($10^4$) were seeded in 100 µl of medium, using 96-well plates. After 24 h, fungal extracts were added in several concentrations: 1, 2.5, 5, 7.5, 10, 25, and 50 µg/ml for 24, 48, and 72 hours. On the day of examination 10 µl of BrdU reagent was added to each well, and the plates were incubated in a $CO_2$ incubator for 4 hours. Next, cells were fixed with 0.5M ethanol/HCL for 30 minutes in −20° C. Afterwards, plates were washed 3 times to remove residue solution. Then, for the denaturation of DNA partly, plates with cells were incubated with nuclease solution for 30 minutes in 37° C. wrapped with parafilm to avoid $CO_2$ leakage from the incubator. DNA synthesis was determined according to the manufacturer's instructions using an Elisa reader (BioTek) at 492 nm wave and subtracted from the reference absorbance at 690 nm. Experiments were repeated 2-5 times independently and conducted in at least 3 replicates. Data are presented as average DNA synthesis percentage of the respective control.

Cell Cycle and Apoptosis Assays

Cell cycle analysis. $10^6$ HPAF-II and PL45 cell was treated with 10 µg/ml *c. striatus* extract for 24 h at the end of that time cells was trypsinized and collected with the growth medium, centrifuged, and washed with PBS and fixed with 70% ethanol for one hour. This was then followed by the incubation with 0.1% NP-40 for 5 minutes in 4° C. and then incubated on ice with 100 µg/ml RNase for 30 minutes. Finally, 50 µg/ml PI was added for 20 minutes. Cell cycle phase distributions were determined by Fluorescence Activated Cell Sorter (FACS) flow cytometry (Becton Dickinson); 10,000 cells were counted for each control and treatment group.

Apoptosis induction. Apoptosis induction was examined biochemically and morphologically.

DNA Fragmentation

Genomic DNA was extracted from treated and untreated control cells of both cell lines. Briefly, at the end of treatment, the cells' medium was collected into 50 ml tubes and cells were trypsinized and added to 50-ml tubes following centrifugation at 2000 rpm. Subsequently, cells were washed with PBS twice and suspended in 1 ml lysis buffer that contains: 0.5% SDS, 0.1 M NaCl, 50 Mm Tris-buffer, 1 mM EDTA, pH=7.5, and 200 µg/ml proteinase K. Next, an eppendorf tube with lysis buffer and cells were incubated at 55° C. overnight. On the next day, samples were mixed with equal volumes of phenol:chloroform:isoamyl alcohol, vortexed for a minute, and centrifuged for 15 minutes at 13,000 rpm. The upper phase was carefully collected into a new eppendorf tube and mixed again with phenol:chloroform:isoamyl. This step was repeated twice. RNAse (5 µl) was added and cells were incubated for 60 minutes at 37° C. Next, phenol:chloroform: isoamyl was repeated following centrifugation at 13,000 rpm for 15 minutes. DNA precipitation was carried out using 0.3 M sodium acetate and ice cold absolute alcohol was added to an equal volume of sample and incubated over night at −20° C. The next day, samples were centrifuged for 15 minutes at 4° C. and 13,000 rpm; all supernatants were removed and samples were left to dry. DNA was re-suspended in dionized $H_2O$ and kept in 37° C. overnight. DNA concentration was determined using Nanodrop. Fragments were observed by gel electrophoresis (1.5% agarose TBEx0.5) using 60V for 3 hours. Gel was analyzed using ChemiDoc XRS (Bio-Rad).

Cell Morphology Characterization

Pancreatic cancer cells (HPAF-II and PL45) were counted ($25 \times 10^3$ cells/ml) and seeded on chamber slides (Nunc, Denmark). The next day, growth medium was replaced with medium containing 10 µg/ml *C. striatus* C.L. EAC extract. After 24 h, cell morphology was examined using DAPI and TUNEL (In Situ Cell Death Detection Kit, Roch) staining Cell growth medium and mushroom extracts were removed, cells were washed twice with PBS, fixed for 60 minutes, and permeabilized. Subsequently, cells were incubated with the TUNEL reaction mixture that contains TdT and fluorescein-dUTP. During this incubation period, TdT catalyzes the addition of fluorescein-dUTP at free 3'-OH groups in single- and double-stranded DNA. After washing, the label incorporated at the damaged sites of the DNA is visualized by fluorescence microscopy. DAPI stain was added on top of TUNEL treated cells.

Annexin V-FITC Staining

Pancreatic cancer cells (HPAF-II and PL45) were treated with different extract concentrations for 4 h, and $5 \times 10^5$ cells/ml were counted and collected for the analysis. Cells were resuspended in 500 µl of 1 X binding buffer, 5 µl of Annexin V-FITC and 5 µl of propidium iodide were added. Cells were incubated for 5 minutes at room temperature in the dark. Cell apoptosis was measured using Annexin V-FITC Apoptosis Detection Kit (MBL, USA) and determined using a BD Facscalibor flow cytometer.

Caspase Activation

The mammalian caspases play distinct roles in apoptosis and inflammation. In apoptosis, caspases are responsible for a proteolytic cleavages that lead to cell disassembly (effector caspases), and are involved in upstream regulatory events (initiator caspases). An active caspase consists of two large (~20 kD) and two small (~10 kD) subunits that form two heterodimers which associate in a tetramer (Nicholson & Thornberry, 1997).

FLICA Apoptosis Detection Kits use a Fluorochrome Inhibitor of Caspases (FLICA). Once inside the cell, the FLICA inhibitor binds covalently to the active caspase enzymes and retained in cells undergoing the process of apoptosis. HPAF-II and PL45 cells ($1 \times 10^6$ cells/ml) were incubated with different concentrations (2.5 or 5 µg/ml) of *C. striatus* extract for 2 or 4 h. At the end of treatment, cells were labeled with FLICA FAM-LETD-FMK for caspase 8 detaction or FLICA FAM-LEHD-FMK for caspase 9 detection using carboxyfluorescein FLICA Apoptosis Detection Kit Caspase Assay (Immunochemistry Technologies, LLC, USA). The green fluorescent signal is a direct measure of the number of active caspase enzymes that were present in the cell at the time the reagent was added. Caspase activity was detected using a BD Facscalibor flow cytometer.

Western Blotting

HPAF-II and PL45 cell lines were induced for 12 h with medium containing the indicated concentrations of *C. striatus* extract. After induction, $2 \times 10^6$ cells were lysed in 0.2 ml RIPA buffer and 20 µl of protease inhibitors stock (×25) per 0.5 ml RIPA buffer was also added, subjected to SDS-PAGE, and blotted with the following antibodies: Caspase-9 and caspase-3 (Cell Signaling Technology, Beverly, Mass.) The detection of immobilized proteins was performed using the EZ-ECL Chemiluminescence Detection Kit for HRP (Biological Industries, Beit-Haemek, Israel) according to manufacturer's instructions. The proteins were visualized using the ChemiDocTMXRS Gel Documentation System (BioRad).

Statistics

All results displayed as means±SE were expressed as percentages of control (XTT, Crystal violet, BrdU). ONE WAY ANOVA was used for the evaluation of the differences between treatment groups and control groups. $P<0.05$ was considered significant, and SPSS software was used for the calculation of differences. All experiments were performed at least three times and with four replicates.

Example 1

A Novel *Cyathus striatus* Strain

Fruit Body 7-15 mm tall, 6-8 mm wide, strongly infundibuliform with narrow, tapering base. PERIDIUM at first entirely covering the gasterocarp then apically fragmenting to reveal the epifragm, outer surface rusty brown to dark fuscous brown, shaggy-tomentose to hairy. Inner surface grayish, vertically ridged or fluted. PERIDIOLES 12-16 in number, 1-2 mm in diam., lenticular, pale grayish each attached by a fine, thread-like funiculus to the inner peridial surface. BASIDIOSPORES 12-21×7.0-12 oblong ellipsoid to ellipsoid, hyaline, smooth, thick-walled. PERIDIOPELLIS of brown, constricted hyphae, with clamp connections, and fusoid terminal elements, 35-75×8-15 µm.

Habitat & General Distribution:

Fruit bodies are gregarious on fallen branches, twigs and other debris, often in large numbers, nearly always in woodland, rarely in gardens. AFRICA: Cameroon. ASIA: and Israel Japan, Korea. AUSTRALASIA: New Zealand. EUROPE: Austria, Belgium, Czech Republic, Denmark, Estonia, France, Germany, Ireland, Italy, Norway, Poland, Portugal, Romania, Slovenia, Spain, Sweden, UK. NORTH AMERICA: Canada, USA. SOUTH AMERICA: Costa Rica, Ecuador, Venezuela.

Vegetative Mycelium in Pure Culture:

The mycelium was at first white, but soon became a dirty brownish color, felty, dense in the center of colony, with many strong mycelial strands. In a few cases small knots appeared upon the mycelium. Clamp connections, crystals, and anastamoses are present on hyphae.

A novel strain was isolated and deposited at Haifa University Culture Collection (HAI) under the name *Cyathus striatus* (HAI-1302). It was also deposited under The Budapest Treaty with the Centralbureau voor Schimmelcultures (CBS (Uppsalalaan 8, P.O. Box 85167 3508 AD UTRECHT, the Netherlands)) under Accession No. CBS 126585 (hereinafter *Cyathus striatus* CBS 126585) on Mar. 29, 2010. The novel strain was isolated as follows:

Fruiting bodies of *Cyathus striatus* were collected from their natural habitat in Israel. The mushroom submerged culture mycelium (SCM) production included 5 steps of culture growth: Museum culture (I)→Intermediate culture (II)→Pre-inoculums culture (III)→Inoculums culture (IV)→Fermentation culture (V).

Morphological characters of *Cyathus striatus* (HAI-1302): Colony dense, first cream, later becoming pale cream-brownish with small exudate drops on aerial mycelium. Around central zone with well developed, dense, downy aerial mycelium. From central zone to edge of margin with radial branched brown hyphae. Margin even, reverse achromatic. Plate covered within one month.

Hyphal characteristics: Marginal mycelium hyphae hyaline to pale brown, brownish pigmented, simple septate, thick to thin-walled, 3.96-5.94 mµ wide, branched. Many clamp connections, anastamoses, and crystals are present.

Example 2

Effect of Selected Mushroom Extract on Cell Viability

Cytotoxicity Assays
XTT assay.

EAC extracts of the mycelial biomass of *C. striatus* and its culture liquid (C.L.) were tested for their ability to affect cell viability (not shown). The *C. striatus* C.L. extract showed a most potent growth-inhibitory effect, which inhibited the growth of HPAF-II and PL45 with $IC_{50}$ of 6 and 4 µg/ml, respectively, for 24 h treatment, 2 µg/ml for both cell lines for 48 h treatment, and 8 and 4 µg/ml for 72 h treatment (not shown).

Figure 1A:
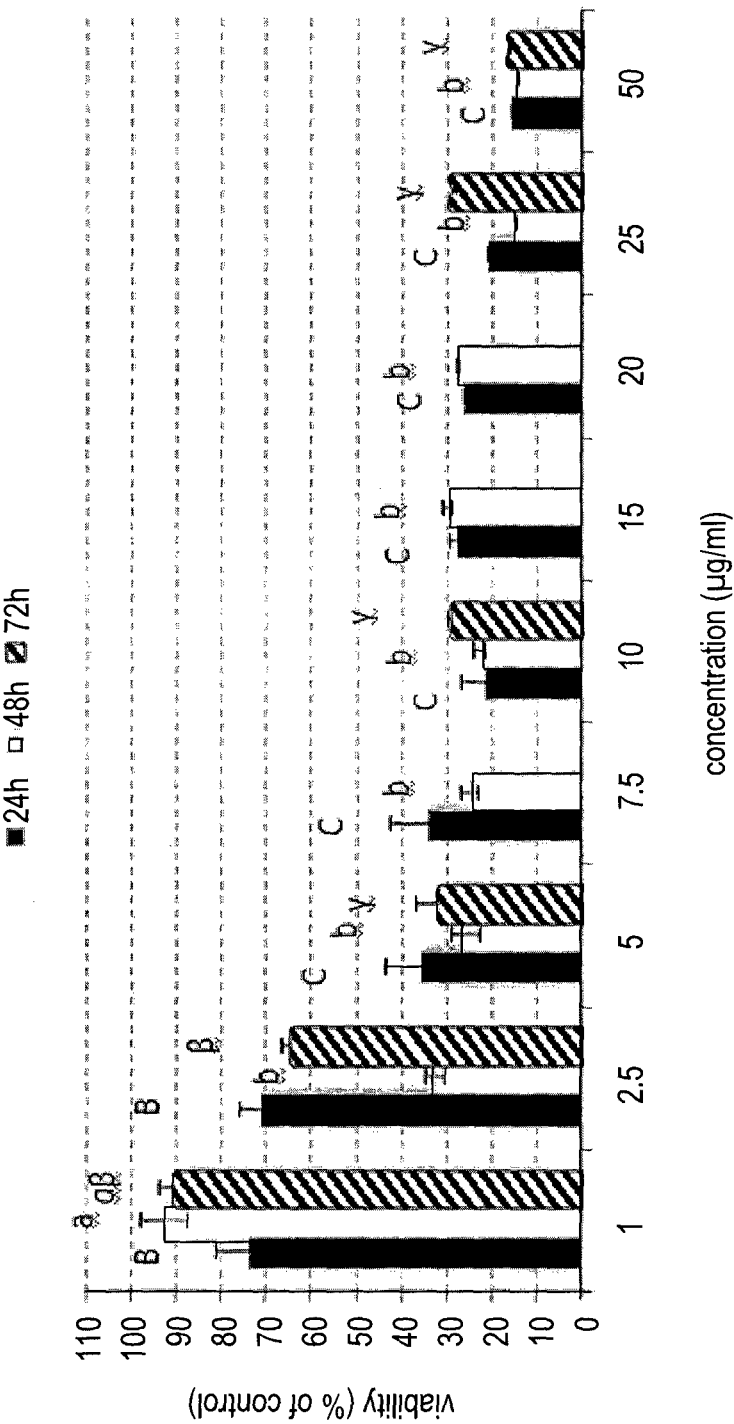
FIGS. 1A-B show the effect of *C. striatus* C.L ethyl acetate (EAC) extract on the viability of (A) HPAF-II and (B) PL45 cells by XTT assay. Cells were seeded in a 96-well plate ($10^4$ cells/ml), after 24 h cells were treated with different extract concentrations and incubated for 24, 48, and 72 hours. At the end of treatment, cell viability was measured using XTT (Biological Industries, Israel). All results presented are an average of three independent experiments: four repeats each (mean±SEM) and expressed as percentages of control (non-treated cells). Statistical significance was determined by one way ANOVA $P<0.05$. Each letter above bars represents relations to fellow concentrations in the same treatment period.
Figure 1B:
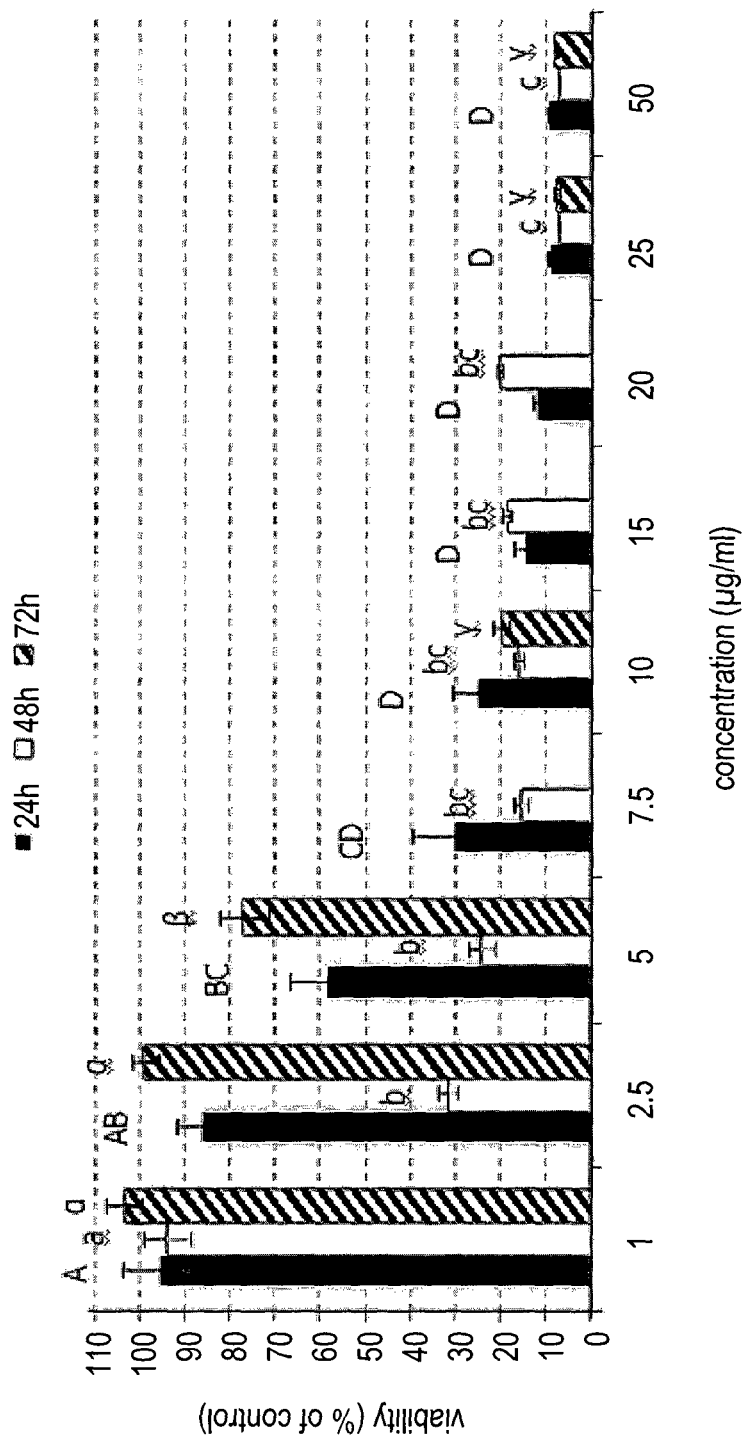

Pancreatic cancer cell lines treated with 10 and 5 µg/ml *C. striatus* C.L. EAC extract for 24 h induced more than 70% reduction in cell viability of HPAF-II and 65% reduction in cell viability of PL45 cells ($f_{(9,81)}$=38.783, p<0.001 and $f_{(9,67)}$=33.626. p<0.001), respectively (FIGS. 1A-B). The decline in cell viability was found to be dose-dependent and the decrease in living cells of the cell line HPAF-II was found significant in all concentrations leave out treatment concentrations of 1 and 2.5 µg/ml. Interestingly, the reduction in cell viability was maximal at 10 µg/ml and it was not further reduced (at 15, 20, 25, and 50 µg/ml). Regarding cell line PL45, the 24 h treatment also induced a decrease in living cells, and the cell viability was not further reduced above concentrations of 5 µg/ml. Treatment for 48 and 72 h produced similar results: a significant decrease in living cells ($f_{(9,94)}$=139.055, p<0.001; $f_{(6,63)}$=182.779, p<0.001) for 48 and 72 h treatment, respectively, for both the cell line HPAF-II and ($f_{(9,109)}$=40.985, p<0.001; $f_{(6,73)}$=27.311, p<0.001) for the cell line PL45. The treatment with concentrations above 5 and 7.5 µg/ml for cell lines HPAF-II and PL45, respectively, induced more than 80% reduction in cell viability that did not change significantly as the concentration increased above those recorded at 48 h treatment. However, treatment for 72 h induced smaller reduction in cell viability; only 50% decline in cell viability was found for cell line HPAF-II. For the cell line PL45 the effect was the same (69-86% for concentrations of 5, 10, 25, and 50 µg/ml).

In all treatment periods (24, 48, and 72 hours) we did not find a significant difference between the effects of treatment with 10 µg/ml *C. striatus* C.L. EAC extract that induced a 70-80% decrease in HPAF-II and PL45 cell lines viability ($f_{(2,35)}$=1.978, p=0.154; $f_{(2,35)}$=0.970, p=0.389), respectively. For this reason, the 10 µg/ml *C. striatus* C.L. extract and 24 h treatment were chosen for further evaluation (FACS, DNA fragmentation, and apoptotic morphology) in spite of the different $IC_{50}$ values. The effect of the extract in the specific concentration (10 µg/ml) was also not found to be significantly different from the effect of higher concentrations (15, 20, 25, and 50 µg/ml) in both cell lines (HPAF-II; $f_{(2,35)}$=1.978, p=0.154 and PL45; $f_{(2,35)}$=0.97, p=0.389).

Crystal Violet Assay.

Figure 2A:
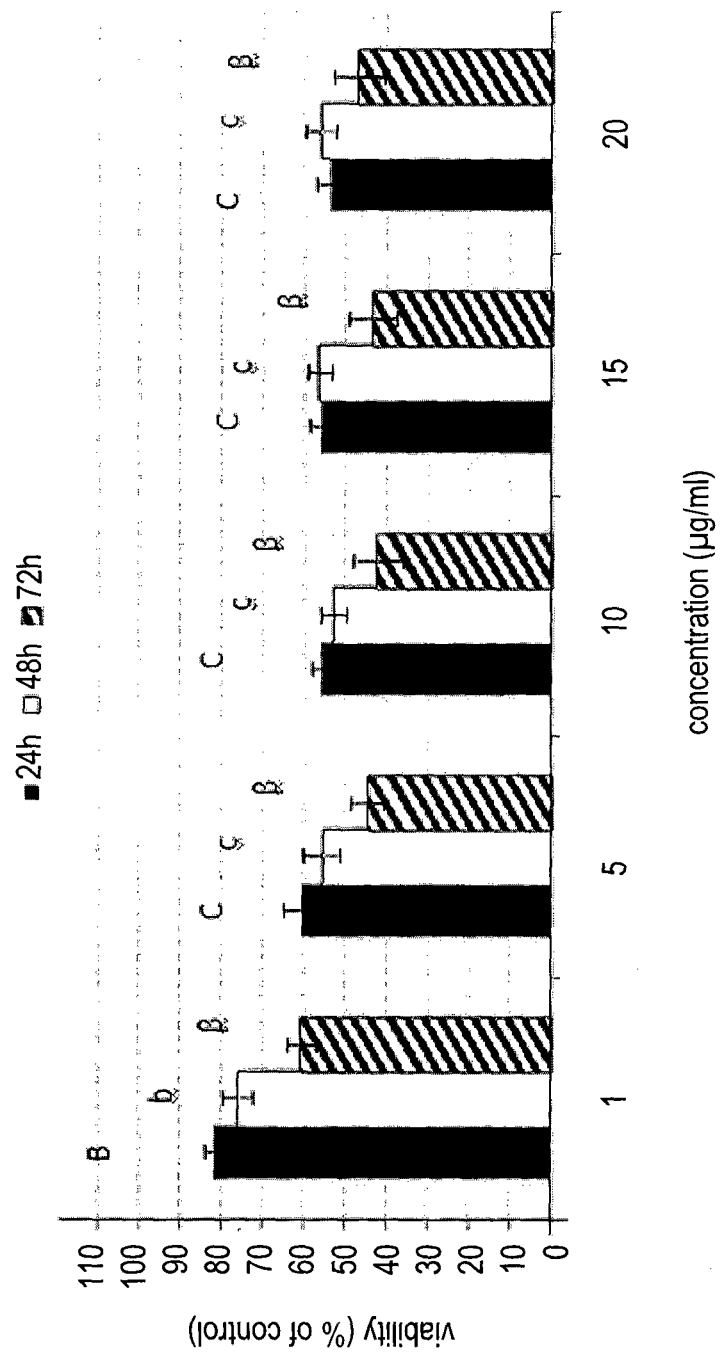
FIGS. 2A-B depict the effect of *C. striatus* C.L EAC on the viability of (A) HPAF-II and (B) PL45 cells by Crystal violet assay. Cells were seeded in a 24-well plate ($5 \times 10^4$ cells/ml). After 24 h, cells were treated with different extract concentrations and incubated for 24, 48, and 72 hours. At the end of treatment, cell viability was measured using the Crystal violet assay (see Example 2, Materials and Methods). All results presented are an average of three independent experiments: four repeats each (mean±SEM) and expressed as percentages of control (non-treated cells). Statistical significance was determined by one way ANOVA $P<0.05$. Each letter above bars represents relations to fellow concentrations in the same treatment period.
Figure 2B:
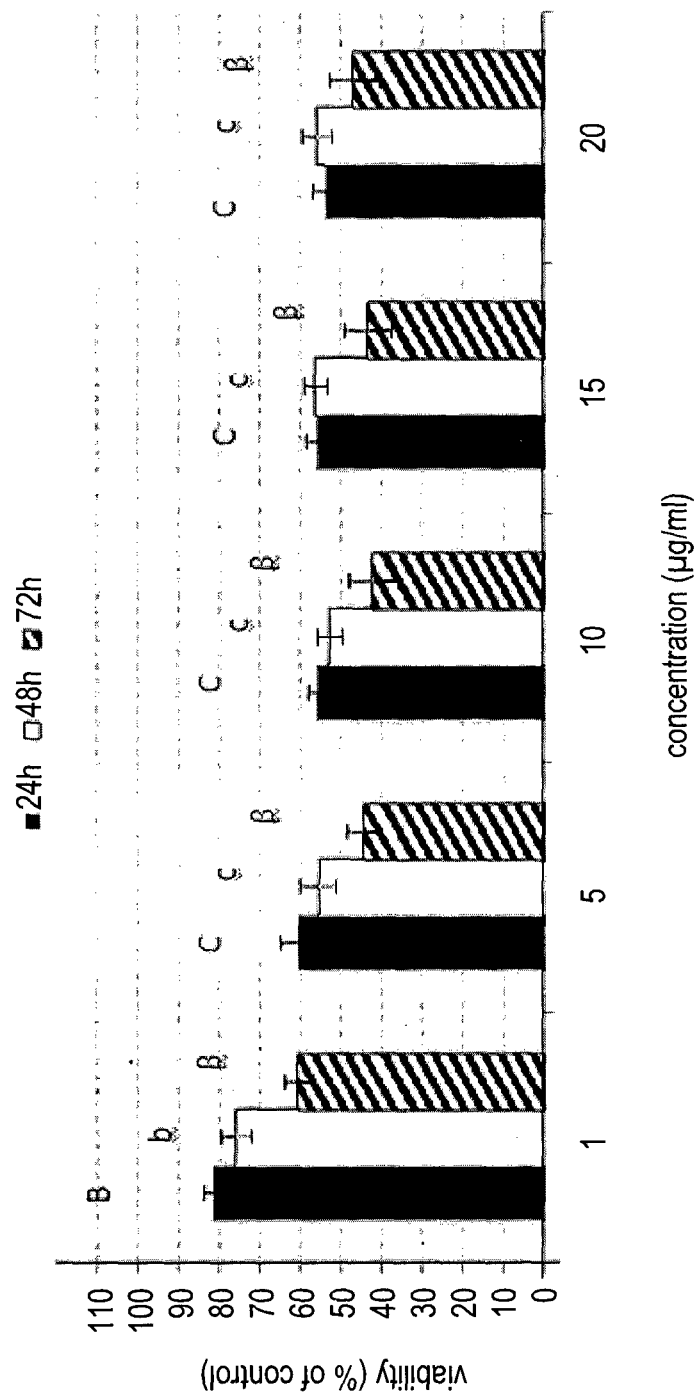

The same trend seen in XTT assays was shown with Crystal violet assay. The Crystal violet results emphasize the finding that there was no significant difference between the effect of 24, 48, and 72 treatment hours with 10 µg/ml of *C. striatus* C.L. EAC extract for cell line HPAF-II (f(2,33)=3.119, p=0.057). For the PL45 cell line, we found a slight difference (p=0.047) between the effect of 24 h treatment with the extract and 72 h treatment (37% and 54% inhibition, respectively). Generally, the reduction in viability ranged between 40-60% for all treatment concentrations and all treatment hours for both cell lines (FIGS. 2A-B).

LDH Leakage.

LDH is a cytoplasmic enzyme constantly expressed in most mammalian cells. It is well accepted to use the amount of LDH in extracellular space to assess plasma membrane integrity (Korzeniewski & Callewaert, 1983). The capability of LDH assay to detect cytotoxic effects is limited to the agents causing direct damage on cellular membranes.

Figure 3:
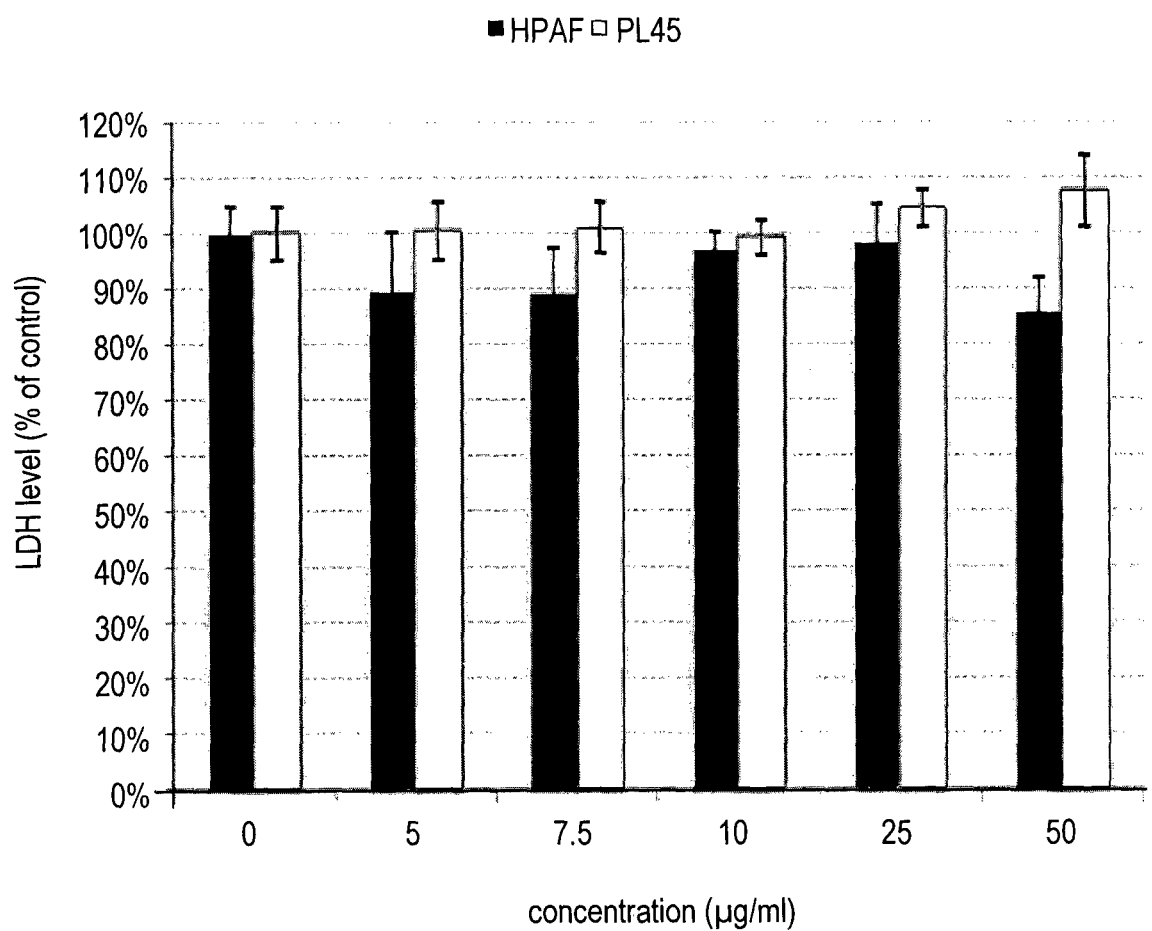
FIG. 3 shows the effect of *C. striatus* C.L EAC on the cytotoxicity of HPAF-II and PL45 cells by LDH leakage. Cells were seeded in a 24-well plate ($5 \times 10^4$ cells/ml). After 24 h, cells were treated with different extract concentrations and incubated for 24 h. At the end of treatment, LDH leakage was measured using a colorimetric assay (see Example 2, Materials and Methods). All results were expressed as percentages of control (non-treated cells).

LDH assay was not able to detect any toxic effects caused by all concentrations exhibited in FIG. 3, and, therefore, *C. striatus* C.L. extract was found not to damage the cell membranes of HPAF-II and PL45 cell lines.

DNA Synthesis.

Notwithstanding, it was apparent that the *C. striatus* C.L. extract impaired the viability of the pancreatic cancer cell lines; the sustained effects on culture growth raised suspicion that it might also affect the proliferation of surviving cells. To test this possibility, we examined whether *C. striatus* C.L. extract hinders DNA synthesis. The effect of the extract on both cell lines was tested by the incorporation of BrdU. DNA synthesis was measured for HPAF-II and PL45 cell lines following 24, 48, and 72 h treatment with different concentrations of the *C. striatus* C.L. extract (1, 2.5, 5, 7.5, 10, 15, and 20 µg/ml).

Figure 4A:
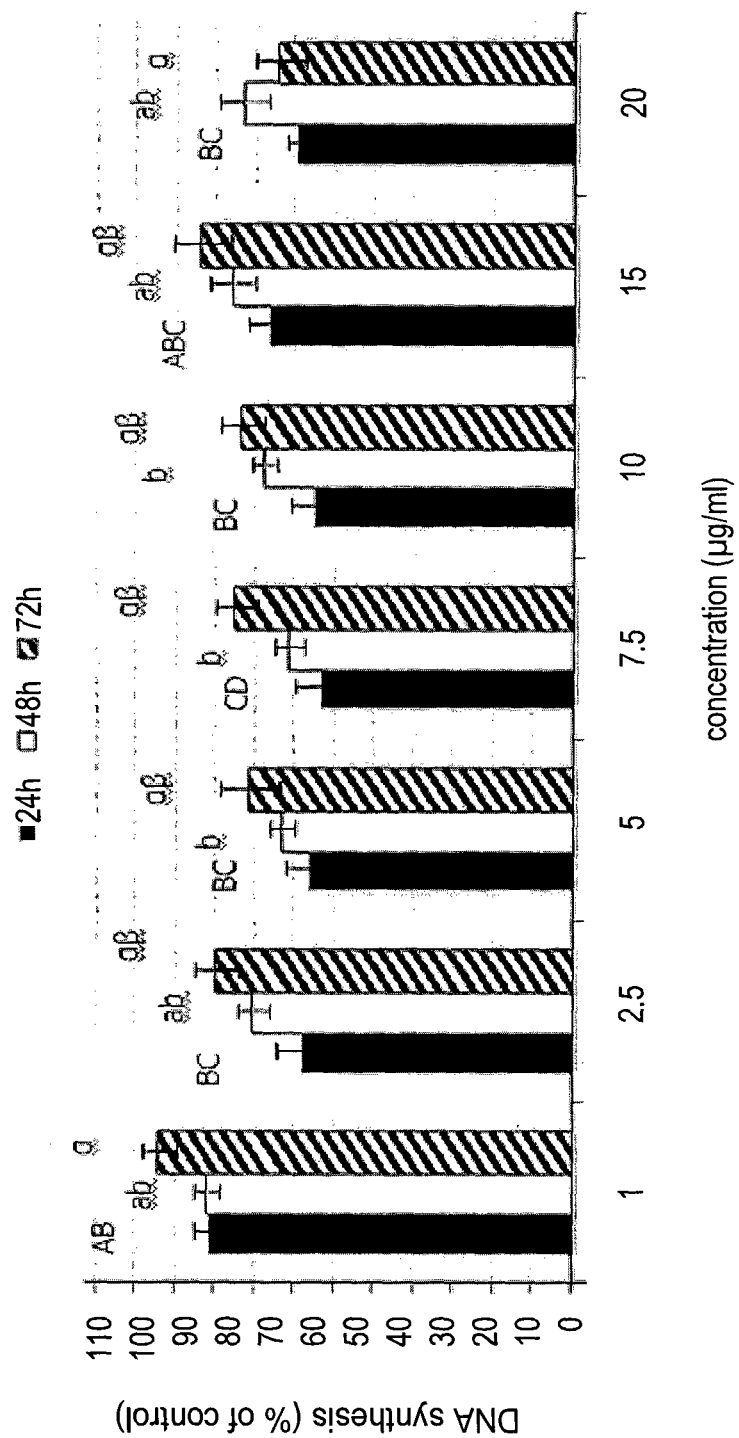
FIGS. 4A-B depict the effect of *C. striatus* C.L EAC on DNA synthesis of (A) HPAF-II and (B) PL45 cells by the BrdU assay (see Example 2, Materials and Method). Cells were seeded in a 96-well plate ($10^4$ cells/ml). After 24 h, cells were treated with different extract concentrations and incubated for 24, 48, and 72 hours. At the end of treatment, cell DNA synthesis was measured using the BrdU assay. All results presented are averages of three independent experiments; four repeats each (mean±SEM) and expressed as percentages of control (non-treated cells). Statistical significance was determined by one way ANOVA $P<0.05$. Each letter above bars represents relations to fellow concentrations in the same treatment period.
Figure 4B:
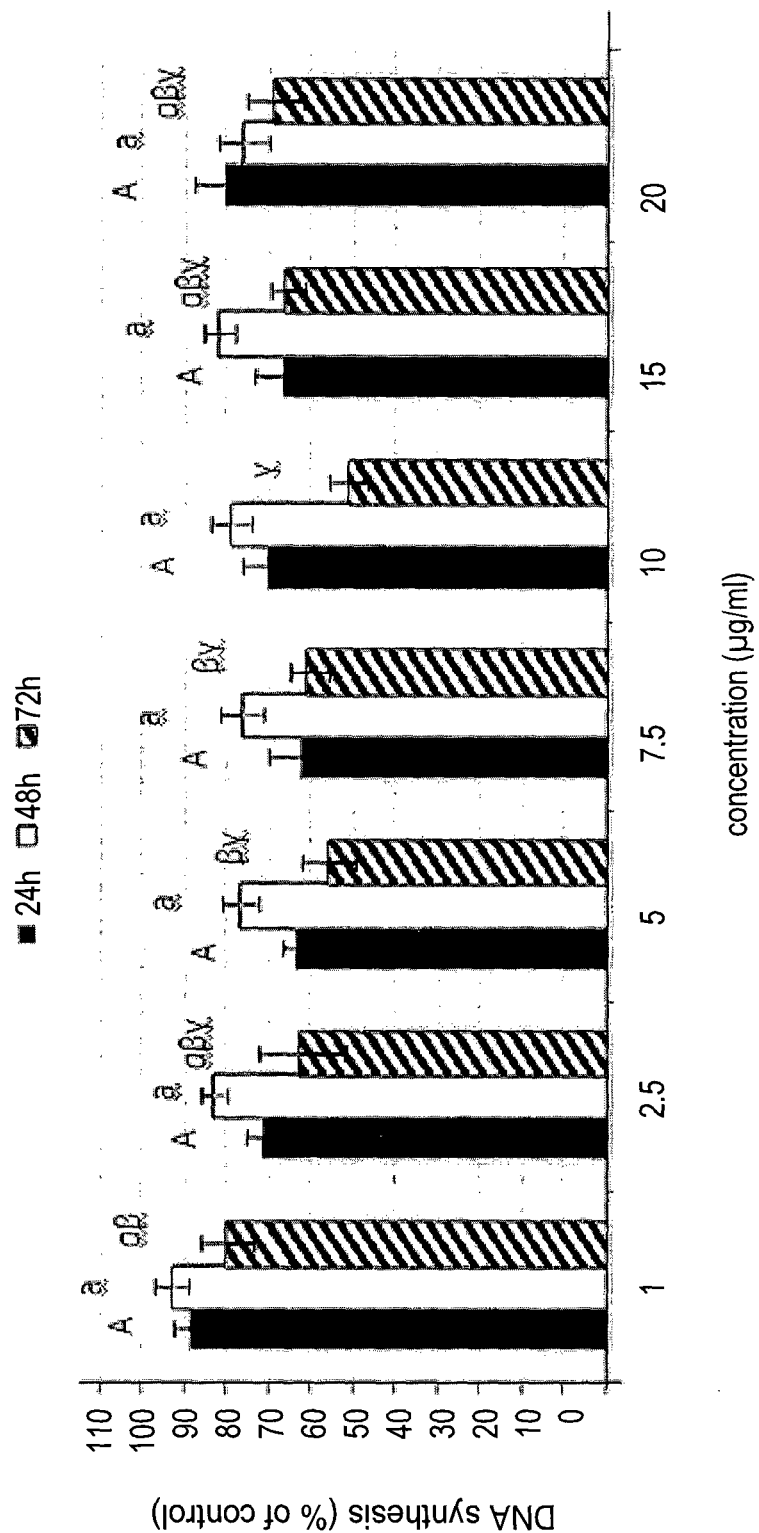
Figure 5A:
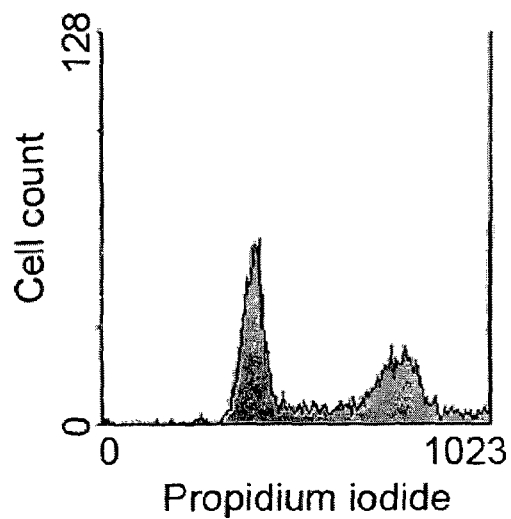
FIGS. 5A-D show the effect of *C. striatus* C.L EAC extract on cell cycle using FACS Flow cytometry analysis. *C. striatus* C.L EAC extract induces cell accumulation in SubG1-phase of the cell cycle in both HPAF-II and PL45 cell lines. Exponentially growing cells were exposed to either medium (control) or *C. striatus* C.L EAC extract (10 μg/ml) for 24 h. Cells were then harvested, washed in PBS, and fixed in 70% ethanol. DNA content was evaluated with propidium iodide staining and fluorescence was measured and analyzed as described in Materials and Methods (Example 2). Data are representative of three independent experiments. (A) HPAF-II control; (B) 24 h 10 μg/ml *C. striatus* C.L EAC extract treatment; (C) PL45 control; (D) 24 h 10 μg/ml *C. striatus* C.L EAC extract treatment. The data shown in the upper right corner of each panel show the relative number (%) of cells found in each phase of the cell cycle (SubG1, G1, S, and G2/M).
Figure 5C:
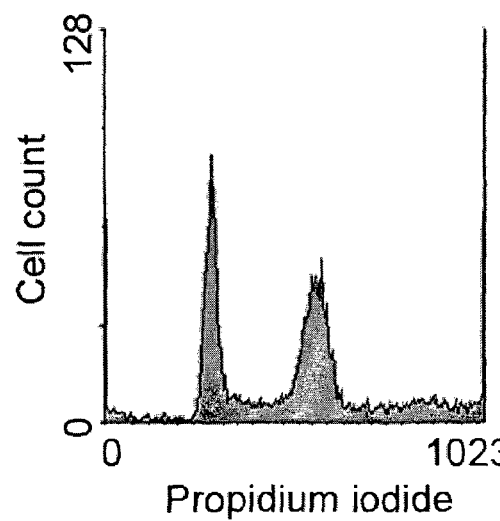
Figure 5B:
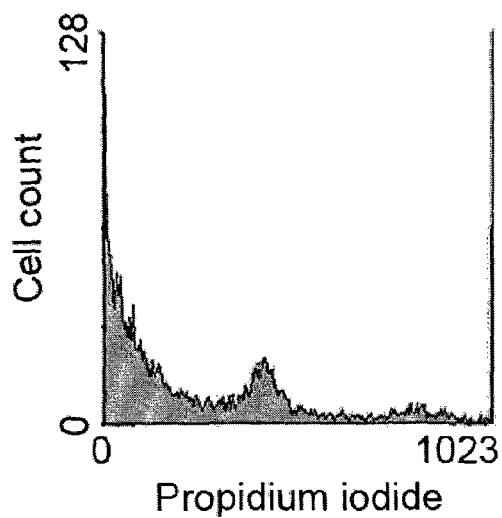
Figure 5D:
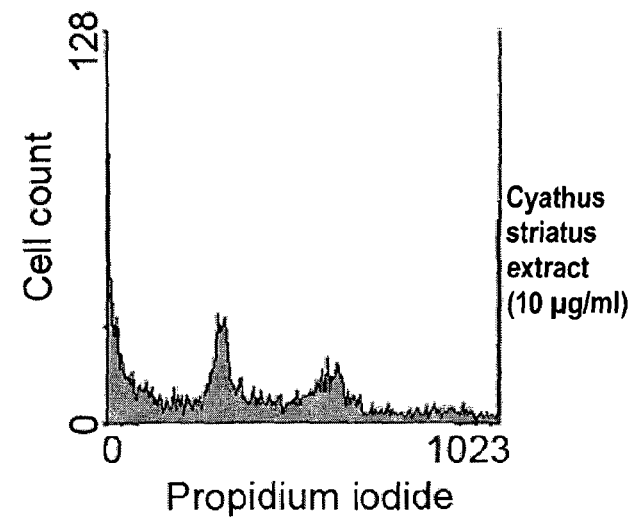

DNA synthesis measurement was conducted to further support the evidence of inhibition of growth induced by the *C. striatus* C.L. extract of HPAF-II and PL45 pancreatic cell lines. A decrease in DNA synthesis as measured by BrdU Labeling Kit for HPAF-II cell line was found to be significant for all treatment hours (24, 48 and 72 hours; $f_{(8,111)}$=7.776, p<0.001; $f_{(7,111)}$=4.130, p<0.001; $f_{(7,84)}$=2.92, p=0.00, respectively) (FIGS. 4A-B). DNA synthesis as measured for HPAF-II cell line was decreased by 35%, 22%, and 16% following 24, 48, and 72 hours treatment, respectively, with 10 µg/ml of *C. striatus* C.L. extract. There was no significant difference among the effects of different treatment hours (p=0.098) at the µg/ml concentration of the extract. For the PL45 cell line, a significant decrease was shown for the same treatment concentration (10 µg/ml) at 24 h ($f_{(8,114)}$=5.857, p<0.001). The synthesis declined by 20% for all treatment concentrations. The treatment at 48 h did not induce a significant reduction in DNA synthesis of treated cells compared to control cells (10.5%). In contrast, 72-h treatment revealed a 40% decrease of DNA synthesis ($f_{(7,84)}$=3.874, p=0.001).

Apoptosis and Cell Cycle Assays
Cell Cycle Analysis.

In order to further evaluate the effect of *C. striatus* C.L. extract on the pancreatic cancer cell lines, we examined whether *C. striatus* C.L. extract affects cell cycle progression. HPAF-II and PL45 cells were treated with 10 µg/ml of *C. striatus* C.L. extract (approximate IC80). As shown in FIG. 5, *C. striatus* C.L. extract caused both cell lines to accumulate in SubG1-phase (47.24% and 26.66% in *C. striatus* C.L. extract treated vs. 0.86% and 2.42% in control HPAF-II and PL45 cells, respectively) within 24 h at the expense of cells mainly in G1 phase for HPAF-II cells and G2/M for PL45 cells. This was associated with the induction of apoptosis as represented by the large sub-G1 peak. On the other hand, induction of apoptosis by *C. striatus* C.L. extract was less dramatic in PL45 cells where cellular accumulation in sub-G1 was slightly lower (26.66%) than HPAF-II cells (47.24%).

DNA Fragmentation.

Figure 6:
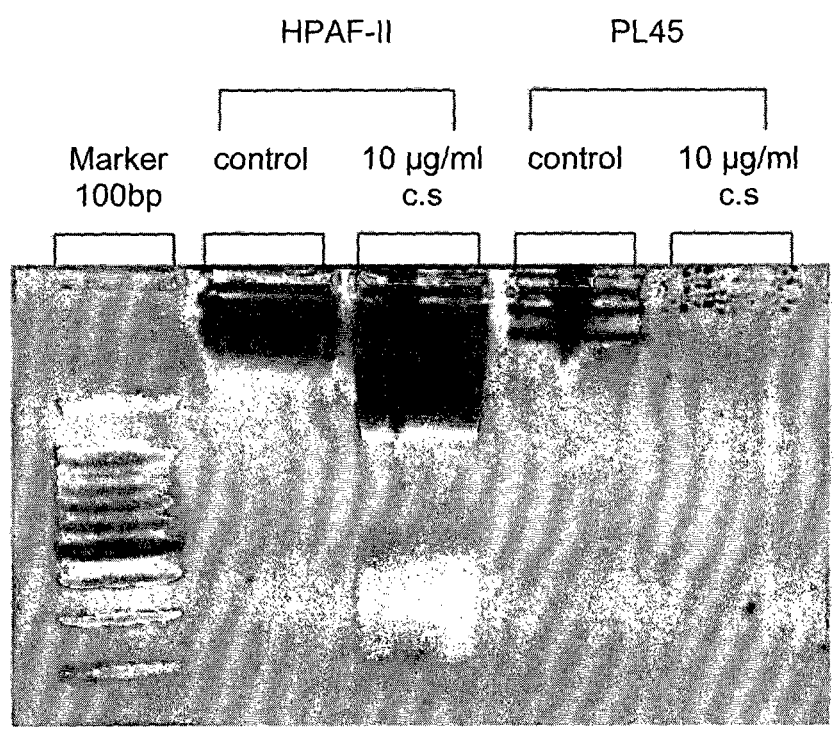
FIG. 6 shows the effect of *C. striatus* C.L EAC extract on apoptosis induction by agarose gel electrophoresis of DNA fragmentation. HPAF-II and PL45 cells were treated with 10 μg/ml *C. striatus* C.L extract (c.s) for 24 h before being harvested. Left to right: Lane 1: DNA marker: 100 bp ladder.

To determine whether the decrease in viable cells occurs after exposure to *C. striatus* C.L. extract we investigated whether the effect of this extract was mediated through the induction of apoptosis. Following treatment with 10 µg/ml of *C. striatus* C.L. extract, DNA was extracted from HPAF-II and PL45 cells and placed onto a 1.5% agarose gel, as described in Materials and Methods. The results presented in FIG. 6 show a DNA ladder in HPAF-II cells after 24 h treatment (a dose causing 75% decrease in cell growth). The typical DNA ladder was observed only for the HPAF-II cell line. For the PL45 cell line there was no obvious fragmentation shown by DNA ladder.

Cell Morphology Characterization.

Apoptotic cells were also characterized by morphological changes such as cell shrinkage and the generation of apoptotic bodies. Cells were counted and seeded on chamber slides (Nunc, Denmark) (25*103 cells/ml). On the next day cells were treated with *C. striatus* C.L. extract for 24 h at a concentration of 10 µg/ml and stained with TUNEL or DAPI. The results in FIG. 7 show treated cells with typical apoptotic morphology, condensation, and fragmentation of the nucleus in comparison to untreated cells.

Annexin V-FITC Staining.

Shortly after initiating apoptosis, most cell types translocate the membrane phospholipid phosphatidylserine (ps) from the inner face of the plasma membrane to the cell surface. Once on the cell surface, ps can be easily detected by staining with a fluorescent conjugate of annexin V, a protein that has a strong natural affinity for ps (koopman et al., 1994; martin et al., 1995). Control untreated cells and cells treated with 2.5, 5, and 10 µg/ml of *C. striatus* extract for 4 h was stained with Annexin V-FITC and propidium iodide and analyzed for Annexin V-FITC binding by flow cytometry.

Flow cytometry-based annexin V apoptosis assay revealed a significant increase in apoptotic cells due to treatment with *C. stiatus* C.L extract. Apoptosis induction in treated HPAF-II and PL45 cells was found to be dose dependent and a dose of 10 µg/ml induced a remarkable effect, 85% of both cell lines displayed a considerable increase compared with the apoptotic ratio of control untreated cells (FIGS. 8A-B). This finding further verifies the results of cell cycle analysis, TUNEL and DAPI staining which also showed a prominent apoptosis induction by the *C. striatus* extract.

Caspase Activation.

Execution of apoptosis relies on a group of cysteine proteases, the caspases (Degterev et al., 2003). To determine whether *C. striatus* extract-induced apoptosis involves the activation of caspase cascade, we examined the activations of caspase-8 (flow cytometry), caspase-9 (flow cytometry and western blotting), and caspase-3 (western blotting). It was found that the activation of caspase-8, and -9 was observed at 2 h after *C. stiatus* extract treatment at a concentration of 2.5 µg/ml. The cell line PL45 exhibited 40% caspase-8 activation in contrast to 11% seen in control untreated cells (FIG. 9B) and 42% caspase-9 activation in contrast to 24% seen in control untreated cells (FIG. 10B). Activation of caspases in HPAF-II treated cells was also observed; 46% caspase-8 activation in contrast to 26% seen in control untreated cells (FIG. 9A), and 57% caspase-9 activation in contrast to 22% seen in control untreated cells were evident after 4 h treatment with 5 µg/ml *C. striatus* extract (FIG. 10A). To further confirm the involvement of caspases in *C. striatus*-induced apoptosis, we examined caspase activation by western blotting also. As shown in FIG. 11, caspase-9 activation occurred in both cell lines. A decrease in pro caspase-9 and an increase in caspase-9 cleaved forms was observed after treatment with different concentrations (2.5, 5, and 10 µg/ml) for 12 h. Western blotting was also performed for caspase-3 activity (FIG. 12); a decrease in pro caspase-3 and an increase in caspase-3 cleaved forms was observed after treatment with different concentrations (2.5, 5, and 10 µg/ml) for 12 h. These results indicate that the caspases play an essential role in *C. striatus*-induced apoptosis in HPAF-II and PL45 pancreatic cancer cells.

Example 3

In Vivo Studies

The anti-cancer activity of the *C. Striatus* C.L EAC extract is investigated in vivo using six-week-old athymic nude male mice (Harlan Laboratories, Indianapolis, USA). Animals are housed in air-conditioned quarters with a 12 h light/dark cycle. Standard chow and water are available ad labium.

The Effect of Extract on Pancreatic Cancer Cell Growth in Animals.

PL45 human pancreatic adenocarcinoma cells are suspended at a concentration of $1\times10^7$ cells/ml medium. 0.1 ml aliquots ($1\times10^6$ cells) are injected subcutaneously into the flank of the mice, using a 27-gauge needle. One week after tumor cell transplantation, the mice are treated 3 times a week by i.p. (intraperitoneal) injection, for three weeks (9 doses), with either saline or *C. Striatus* C.L EAC extract. Tumor size is measured biweekly with a digital caliber and the volumes are calculated using the formula length×width×0.52 (Sauter et al., 2000). At the end of the treatment period, the mice are sacrificed; tumors are collected, weighed, measured, and tested for histological studies. Blood samples are collected from the mice for analysis of liver and kidney function also.

Histological Studies.

Tumors from control and treated groups are kept in formalin, and paraffin blocks are prepared. Four-micron sections are cut and fixed onto slides for histological staining.

Ki-67 Staining.

Examination of cell proliferation in the tumor is conducted using an immunohistochemical reaction with anti-mouse Ki-67 antigen antibody, according to the manufacturer's instructions. Ki-67 is a large nuclear protein, preferentially expressed during all active phases of the cell cycle ($G_1$, S, $G_2$, and M), but absent from resting cells ($G_0$). The proliferation index of the cells is determined in the central and peripheral areas of the tumors. The index is calculated as the ratio of Ki-67-positive tumor cells to all counted tumor cells×100. The results are presented as the mean±SE, calculated according to the cell number in three different fields at ×400 magnification.

DAPI and TUNEL Staining.

DAPI is a fluorescent compound that specifically binds to the DNA and creates a stable complex providing a 20-fold higher fluorescence than DAPI alone, and allows visualization of DNA morphology. DAPI staining of the slides is conducted as described previously (Almog et al., 2002). Tunel (in situ cell death detection kit, Roch) is used to measure and quantitate cell death (apoptosis) by labeling and detection of DNA strand breaks in individual cells. During apoptosis, DNAse activity introduces strand breaks ("nicks") into the DNA. The assays use an optimized terminal transferase (TDT) to label free 3'OH ends in genomic DNA with TMR-dUTP. Slides are photographed using a fluorescence microscope at ×200 magnifications.

REFERENCES

Debatin, K. M. & Krammer, P. H. (2004) Death receptors in chemotherapy and cancer. *Oncogene*, 23:2950-2966

Degterev, A., Boyce, M. & Yuan, J. (2003) A decade of caspases. *Oncogene*, 22:8543-8567.

Fas, S. C., Fritzsching, B., Suri-Payer, E. & Krammer, P. H. (2006). Death receptor signaling and its function in the immune system. *Curr Dir Autoimmun*, 9:1-17

Goeptar, A. R., Groot E. J., Scheerens H., Commandeur J. N., & Vermeulen N. P. (1994) Cytotoxicity of mitomycin C and adriamycin in freshly isolated rat hepatocytes: the role of cytochrome P450. *Cancer Res.* 54:2411-2418

Hager, J. H., & Hanahan, D. (1999) Tumor cells utilize multiple pathways to down-modulate apoptosis. Lessons from a mouse model of islet cell carcinogenesis. *Ann N Y Acad Sci*, 887:150-163

Hezel, A. F., Kimmelman, A. C., Stanger, B. Z., Bardeesy, N. & Depinho, R. A. (2006) Genetics and biology of pancreatic ductal adenocarcinoma. *Genes Dev*, 20:1218-1249.

Ikekawa, T. (2001) Beneficial effects of edible and medicinal mushrooms in health care. *Int J Med Mushr,* 3:291-298

Kang, H. S., Jun, E. M., Park, S. H., Heo, S. J., Lee, T. S., Yoo, I. D. & Kim, J. P. (2007) Cyathusals A, B, and C, antioxidants from the fermented mushroom *Cyathus stercoreus. J Nat Prod* 70:1043-1045

Koopman, G., Reutelingsperger, C. P. M., Kuijten, G. A. M., Keehnen, R. M. J., Pals, S. T. & van Oers M. H. J. (1994) Annexin V for Flow Cytometric Detection of Phosphatidylserine Expression on B Cells Undergoing Apoptosis. *Blood* 84:1415-1420.

Korzeniewski, C. & Callewaert, D. M. (1983) An enzyme-release assay for natural cytotoxicity. *J. Immunol. Methods* 64: 313

Liu, Y. J. & Zhang, K. Q (2003) Antimicrobial activities of selected *Cyathus* species, *Mycopath*, 157: 185-189.

Lu, Q. Y., Sartippour, M. R., Brooks, M. N., Zhang, Q., Hardy, Go, V. L., Li, F. P. & Heber, D. (2004) *Ganoderma Lucidum* spore extract inhibits endothelial and breast cancer cells in vitro. *Oncology reports,* 12:659-662

Maitra, A. & Hruban, R. H. (2008) Pancreatic Cancer. *Annu Rev Pathol,* 3:157-188.

Martin S J, Reutelingsperger C P, McGahon A J, Rader J A, van Schie R C, LaFace D M, Green D R. (1995) Early redistribution of plasma membrane phosphatidylserine is a general feature of apoptosis regardless of the initiating stimulus: inhibition by overexpression of Bcl-2 and Abl. J Exp Med. 1995 Nov. 1; 182(5):1545-56.

Mizuno, T. (1999) The extraction and development of antitumoractive polysaccharides from medicinal mushrooms in Japan. *Int J Med Mushr,* 1:9-29

Moran, J. H. & Schnellmann, R. G. 1996. A rapid beta-NADH-linked fluorescence assay for lactate dehydrogenase in cellular death. *J Pharmacol Toxicol Methods.* 36:41-44.

Muller, C. I., Kumagai, T., O'kelly, J., Seeram, N. P., Heber, D., & Koeffler, H. P. (2006) *Ganoderma lucidum* causes apoptosis in leukemia, lymphoma and multiple myeloma cells. *Leuk Res,* 30:841-848

Nicholson, D. W. & Thornberry, N. A. 1997. Caspases: killer proteases. *Trends Biochem. Sci.* 22:299-306

Okada, H. & Mak, T. W. (2004) Pathways of apoptotic and non-apoptotic death in tumour cells. *Nat Rev Cancer,* 4:592-603

Petrova R. D., Mahajna, J., Reznick, A Z., Wasser, S. P., Denchev, C. M. & Nevo E. (2007) Fungal substances as modulators of NF-jB activation pathway. *Mol Biol Rep,* 34:145-154

Schneider, G., Saur, D., & Schmid, R. M. (2007) Pancreatic cancer—Molecular alterations. *The Chinese-German Journal of Clinical Oncology,* 6:102-106

Schulze-Bergkamen, H. & Krammer, P. H. (2004) Apoptosis in cancer—implications for therapy. *Semin Oncol,* 31:90-119

Smith, J. E., Rowan, N. J., & Sullivan, R. (2002) Medicinal mushrooms: their therapeutic properties and current medical usage with special emphasis on cancer treatments. *Cancer Research UK University of Strathclyde, Glasgow*

Wajant, H. (2006). CD95L/FasL and TRAIL in tumour surveillance and cancer therapy. *Cancer Treat Res,* 130:141-165

Wang, M. W., Hao, X. & Chen, K. (2007) Biological screening of natural products and drug innovation in China. *Phil. Trans. R. Soc. B,* 362:1093-1105

Wasser, S. P., and Weis, A. L. (1999a) Medicinal properties of substances occurring in higher Basidiomycetes mushrooms: current perspectives (Review). *Int J Med Mushr,* 1:31-62

Wasser, S. P., and Weis, A. L. (1999b) Therapeutic effects of substances occurring in higher Basidiomycetes mushrooms: a modern perspective. *Crit Rev Immunol,* 19:65-96

Wu, J. Y., Zhang, Q. X., and Leung, P. H. (2006) Inhibitory effects of ethyl acetate extract of Cordyceps sinensis mycelium on various cancer cells in culture and B16 melanoma in C57BL/6 mice. *Phytomedicine,* 14:43-49

Yassin M, Mahajna J A and Wasser S P (2003) Submerged cultured mycelium extracts of higher Basidiomycetes mushrooms selectively inhibit proliferation and induce differentiation of K562 human chronic myelogenous leukemia cells. *Int J Med Mushr* 5: 261-276.

Zaidman, B., Yassin, M., Mahajna, J., and Wasser, S. P. (2005) Medicinal mushroom modulators of molecular targets as cancer therapeutics. *Appl Microbiol Biotechnol,* 67(4):453-468

The invention claimed is:

1. An extract obtained from *Cyathus striatus* HAI-1302, deposited under The Budapest Treaty with the Centralbureau voor Schimmelcultures (CBS) under Accession No. CBS 126585 (hereinafter *Cyathus striatus* CBS 126585), wherein the extract is obtained by extracting the *Cyathus striatus* CBS 126585 with one or more organic extraction solvents.

2. The extract according to claim 1, wherein said organic extraction solvent is ethyl acetate.

3. The extract according to claim 2, wherein the extract is rich in low-molecular weight compounds such as alkaloids, terpenoids, glycosides, flavonoids, terpenes and phenols.

4. The extract according to 1, wherein the extract (a) inhibits growth of cancer cells; (b) arrests cancer cell cycle; (c) reduces DNA synthesis in cancer cells; and/or (d) induces apoptosis in cancer cells.

5. A method for treatment of cancer comprising administering to a patient in need thereof a therapeutically effective amount of an extract obtained from *Cyathus striatus* CBS 126585, wherein the extract is obtained by extracting the *Cyathus striatus* CBS 126585 with one or more organic extraction solvents.

6. The method according to claim 5, wherein said cancer is selected from pancreatic cancer, breast cancer, chronic myelogenous leukemia (CML) and prostate cancer.

7. The method according to claim 6, wherein said pancreatic cancer is selected from the group consisting of ductal adenocarcinomas, acinar cell carcinomas, adenosquamous carcinomas, colloid carcinomas, giant cell tumors, hepatoid carcinomas, intraductal papillary-mucinous neoplasms, mucinous cystic neoplasms, pancreatoblastomas, serous cystadenomas, signet ring cell carcinomas, solid and pseudopapillary tumors, undifferentiated carcinomas, undifferentiated carcinomas with osteoclast-like giant cells, and pancreatic endocrine tumors.

8. A pharmaceutical composition comprising a pharmaceutically acceptable carrier and an extract obtained from *Cyathus striatus* CBS 126585, wherein the extract is obtained by extracting the *Cyathus striatus* CBS 126585 with one or more organic extraction solvents.

9. The method of claim 6, wherein said cancer is pancreatic cancer.

10. The method according to claim 5, wherein said organic extraction solvent is ethyl acetate.

\* \* \* \* \*

UNITED STATES PATENT AND TRADEMARK OFFICE
CERTIFICATE OF CORRECTION

PATENT NO. : 8,871,197 B2
APPLICATION NO. : 13/701673
DATED : October 28, 2014
INVENTOR(S) : Fares et al.

Page 1 of 1

It is certified that error appears in the above-identified patent and that said Letters Patent is hereby corrected as shown below:

On the Title Page:

Item (75), line 1, Inventor's name, delete "Shavit" and replace it with --Sharvit--.

Signed and Sealed this
Thirty-first Day of March, 2015

Michelle K. Lee
*Director of the United States Patent and Trademark Office*